US009895224B2

(12) United States Patent
Börtlein et al.

(10) Patent No.: US 9,895,224 B2
(45) Date of Patent: Feb. 20, 2018

(54) TREATMENT CATHETER SYSTEM

(75) Inventors: Georg Börtlein, Paris (FR); Malek Nasr, Paris (FR)

(73) Assignee: HIGHLIFE SAS, Paris (FR)

( * ) Notice: Subject to any disclaimer, the term of this patent is extended or adjusted under 35 U.S.C. 154(b) by 919 days.

(21) Appl. No.: 14/343,266

(22) PCT Filed: Sep. 12, 2012

(86) PCT No.: PCT/EP2012/067801
§ 371 (c)(1),
(2), (4) Date: Mar. 25, 2014

(87) PCT Pub. No.: WO2013/037805
PCT Pub. Date: Mar. 21, 2013

(65) Prior Publication Data
US 2015/0238314 A1      Aug. 27, 2015

Related U.S. Application Data

(60) Provisional application No. 61/607,073, filed on Mar. 6, 2012, provisional application No. 61/543,352, filed on Oct. 5, 2011.

(30) Foreign Application Priority Data

Sep. 12, 2011    (DE) .......................... 10 2011 053 528
Oct. 4, 2011     (DE) .......................... 10 2011 054 176
Mar. 6, 2012     (DE) .......................... 10 2012 101 877

(51) Int. Cl.
*A61F 2/24*           (2006.01)
*A61M 25/00*      (2006.01)
(Continued)

(52) U.S. Cl.
CPC ............ *A61F 2/2427* (2013.01); *A61B 17/00* (2013.01); *A61F 2/2466* (2013.01);
(Continued)

(58) Field of Classification Search
CPC .... A61F 2/2457; A61F 2/2427; A61F 2/2466; A61F 2/2455; A61F 2/243; A61F 2/24;
(Continued)

(56) References Cited

U.S. PATENT DOCUMENTS

| 8,409,273 B2* | 4/2013 | Thornton ............... A61B 50/30 606/148 |
| 2002/0013571 A1* | 1/2002 | Goldfarb ............... A61B 17/12 606/1 |

(Continued)

FOREIGN PATENT DOCUMENTS

WO    WO 2009/155561 A2    12/2009

OTHER PUBLICATIONS

Jan. 16, 2013 Written Opinion issued in International Patent Application No. PCT/EP2012/067801.

*Primary Examiner* — Diane Yabut
*Assistant Examiner* — Erich Herbermann
(74) *Attorney, Agent, or Firm* — Oliff PLC

(57) ABSTRACT

A treatment catheter system for treatment of a heart valve includes a circumferential valve tissue structure and an elongate catheter member, and has an inner lumen, proximal and distal end portions. The system includes a catching component which can be positioned at the distal end portion of the catheter member to be non-separable from the catheter member. An outer member extends circumferentially around the catheter member. The circumferential valve tissue structure is correspondingly arranged between the catheter member and the outer member. A catching mechanism reduces a radial distance between the catheter member and the outer member to catch the valve tissue between the outer member and the catheter member via a catching opening to immobilize and treat the caught valve tissue on the distal end portion of the catheter member.

26 Claims, 14 Drawing Sheets

(51) Int. Cl.
  *A61N 1/32* (2006.01)
  *A61B 17/00* (2006.01)
  *A61N 1/30* (2006.01)

(52) U.S. Cl.
  CPC ............ *A61M 25/0082* (2013.01); *A61B 2017/00243* (2013.01); *A61B 2017/00783* (2013.01); *A61B 2017/00867* (2013.01); *A61F 2/2445* (2013.01); *A61F 2/2457* (2013.01); *A61F 2250/0059* (2013.01); *A61M 25/0074* (2013.01); *A61M 2025/0089* (2013.01); *A61M 2025/0096* (2013.01); *A61N 1/306* (2013.01); *A61N 1/327* (2013.01)

(58) Field of Classification Search
  CPC .... A61F 2/2403; A61F 2/2409; A61F 2/2412; A61F 2/2418; A61F 2/2421; A61F 2/2433; A61F 2/2436; A61F 2/2439; A61F 2/2442; A61F 2/2445; A61F 2/2448; A61F 2/2451; A61F 2250/0059; A61M 2025/0096; A61M 2025/0089; A61M 25/0082; A61M 25/0074; A61N 1/327; A61N 1/306; A61B 2017/00783; A61B 2017/00867; A61B 2017/00243
  See application file for complete search history.

(56) References Cited

U.S. PATENT DOCUMENTS

2010/0036481 A1* 2/2010 Dubrul .................. A61F 2/958
                                                              623/1.42
2010/0256751 A1* 10/2010 Rowe .................... A61F 2/2418
                                                              623/2.11

* cited by examiner

TREATMENT CATHETER SYSTEM

The present application claims priority and benefit of U.S. provisional application No. 61/543,352, of German patent application No. 10 2011 054 176.4, of German patent application DE 10 2011 053 528.4, of U.S. provisional application No. 61/607,703, and of German patent Application 10 2012 101 877.4, the whole content of which applications is incorporated hereinto by reference.

TECHNICAL FIELD

Embodiments generally relate to a treatment catheter system comprising a catheter member and an outer member and to a method of using a treatment catheter system.

BACKGROUND

Heart valve diseases are affecting approximately 300,000 people worldwide each year. Those diseases translate in abnormal leaflet tissue (excess tissue growth, tissue degradation/rupture, tissue hardening/calcifying), or abnormal tissue position through the cardiac cycle (i.e. annular dilation, ventricular reshaping) leading to a degrading valve function like leakage/blood backflow (valve insufficiency) or a resistance to blood forward flow (valve stenosis).

Those diseases can be treated mostly by a surgical approach on a stopped heart requiring the use of a heart lung machine and in many cases by an invasive procedure. Some patients due to their general health status may be at higher risk or even contra-indicated for open heart surgery and may benefit from a treatment on a beating heart by catheter techniques.

Accordingly, a treatment catheter system, which allows interaction with tissue on a beating heart, is desirable.

SUMMARY

Various embodiments provide a treatment catheter system for treatment of a bloodstream valve, such as a heart valve, having a circumferential valve tissue structure, comprising an elongate catheter member, for example an elongate flexible catheter member, to be disposed at the interior of the circumferential valve tissue structure and to be removed therefrom after treatment, wherein the catheter member extends along a longitudinal axis and has an inner lumen and proximal and distal end portions, and wherein the catheter member comprises a catching component which is or can be positioned at the distal end portion of the catheter member to be non-separable from the catheter member at least when being positioned at the distal end portion of the catheter member and which at least when being positioned at the distal end portion of the catheter member comprises a lateral groove which extends transverse to the longitudinal axis and which opens to a lateral outer side to form a lateral catching opening, an elongate flexible outer member to be disposed at the exterior of the valve structure at a level of the lateral groove, wherein the outer member can at least partially extend circumferentially around the catheter member with valve tissue of the circumferential valve tissue structure being correspondingly circumferentially arranged between the catheter member and the outer member, and a catching mechanism operable by an interventional cardiologist or a surgeon and allowing reduction or increase of a radial distance between the catheter member and the outer member to catch at least part of the valve tissue between the outer member and the catheter member within the lateral groove via the catching opening to thereby immobilize the caught valve tissue on the distal end portion of the catheter member.

Embodiments of the invention further provide a method for surgical treatment of a bloodstream valve comprising a circumferential valve tissue structure of a patient using a treatment catheter system comprising a catheter member having a longitudinal axis and a lateral groove, and an elongate outer member, the method comprising placing the lateral groove of the catheter member in an interior of the circumferential valve tissue structure, placing the elongate outer member at least partially around an outside of the circumferential tissue structure at an axial level, with respect to the longitudinal axis, of the lateral groove, reducing a distance between the elongate outer member and the lateral groove to at least partially force tissue of the circumferential valve tissue structure into the lateral groove, and removing the catheter member and the elongate outer member from the patient.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which.

DESCRIPTION

Figure 1:
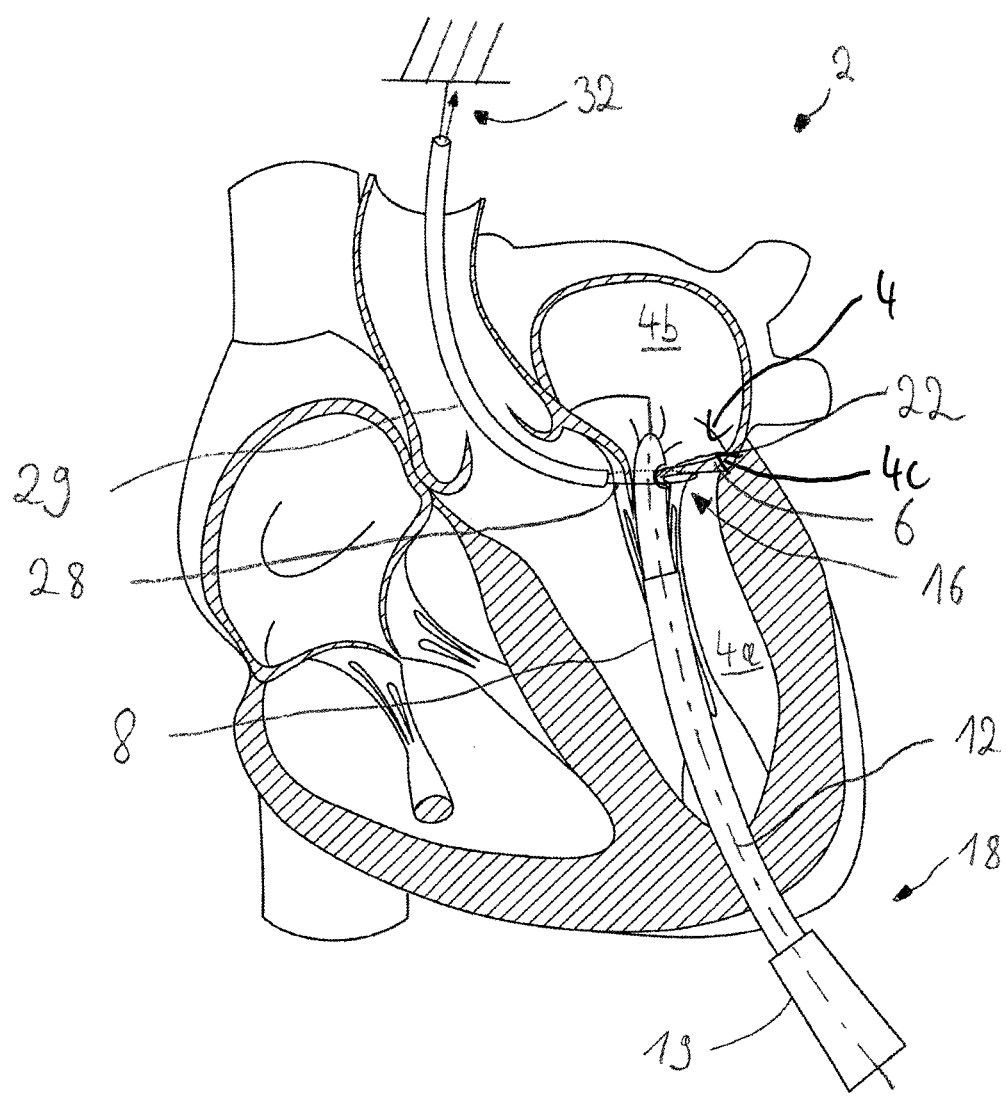
FIG. 1 shows a treatment catheter system according to an embodiment in a partially cut schematic view.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

With reference to the figures, a treatment catheter system 2 for treatment of a heart valve 4 having a circumferential valve tissue structure 6 according to an embodiment comprises an elongate catheter member 8 to be disposed at the interior 10 of the circumferential valve tissue structure 6 and to be removed therefrom after treatment of the heart valve 4, wherein the catheter member 8 extends along a longitudinal axis 12 and has an inner lumen 14 (cf. for example FIG. 2) and proximal 18 and distal 16 end portions, wherein the distal end portion 16 is to be disposed inside of a human or animal body, and the proximal end portion 18, for example, may be kept outside of the human or animal body and may be connected to a handle 19 for being manually operable, for example by an interventional cardiologist or a surgeon, and wherein the catheter member 8 comprises a catching component 20 which is or can be positioned at the distal end portion 16 of the catheter member 8 to be non-separable from the catheter member 8 at least when being positioned at the distal end portion 16 of the catheter member 8 and which at least when being positioned at the distal end portion 16 of the catheter member 8 comprises a lateral groove 22 which extends transverse to the longitudinal axis 12 and which opens to a lateral outer side 24 to form a lateral catching opening 26. The lateral groove 22 may be axially spaced apart from an end of the proximal and/or distal end portions 17, 18. The lateral groove 22 may be formed by a substantially smooth surface geometry, i.e. the lateral groove 22 and the catching opening 26 may not include any hooks or barbs or protrusions or projections or other features that might interfere (e.g. penetrate) with tissue in the lateral groove 22.

The heart valve 4 may have a circumferential tissue structure 6 and an annulus 4c. The heart valve may be connecting two heart chambers (e.g. ventricular chamber 4a and atrial chamber 4b) and an axial direction 4d (c.f double arrow 4d in FIG. 13b) of the valve 4 may be defined between the two chambers the valve is connecting.

The treatment catheter system 2 further comprises an elongate flexible outer member 28 to be disposed at the exterior 30 of the circumferential valve tissue structure 6 at a level of the lateral groove 22, wherein the elongate flexible outer member 28 may at least partially extend circumferentially around the catheter member 8 with valve tissue of the circumferential valve tissue structure 6 being correspondingly (at least partially) circumferentially arranged between the catheter member 8 and the elongate flexible outer member 28.

The treatment catheter system 2 further comprises a catching mechanism 32 (which, for example, includes the lateral groove 22 and the elongate flexible outer member 28) operable, for example, manually operable by an interventional cardiologist or a surgeon, to reduce a radial distance D1 (cf. for example FIG. 7) between the catheter member 8 and the elongate flexible outer member 28 to catch at least part of the valve tissue between the elongate flexible outer member 28 and the catheter member 8 within the lateral groove 22 via the catching opening 26 to thereby immobilize the caught valve tissue on the distal end portion 16 of the catheter member 8. The catching mechanism 32 may also be operable to increase the radial distance D1 in order to facilitate a removal of the elongate flexible outer member 28 and the catheter member 8. The elongate flexible outer member 28 may also remain around the valve tissue, wherein the elongate flexible outer member 28 may be of a self-disruptive material. The elongate flexible outer member 28 may also be cut after treatment to thereby remove the engagement between the elongate flexible outer member 28 and the valve tissue (at least partially) circumferentially engaged by the elongate flexible outer member 28.

As mentioned above, in FIG. 1 the treatment catheter system 2 according to an embodiment is illustrated in a state when being applied to the mitral valve as the heart valve 4 to be caught, immobilized and treated. However, the treatment catheter system 2 may also be applied to other heart valves, such as for the tricuspid valve and/or for the aorta valve and/or for the pulmonic valve. Further, the treatment catheter system 2 may also be applied to other hollow body tissue structure allowing to be correspondingly caught between the inner flexible catheter member 8 and the elongate flexible outer member 28.

The elongate flexible outer member 28 may be a wire or a thread or a chain or any other appropriate elongate flexible means allowing to be guided around the circumferential valve tissue structure. The elongate flexible outer member 28 can also be a hollow component enabling supply of a substance to the valve 4 or surrounding tissue. The elongate flexible outer member 28 may be disposed completely around the circumferential valve tissue structure 4 to form a closed ring therearound. However, the elongate flexible outer member 28 may also be in the shape of an open ring in as far as it is able to force the valve tissue to be caught in the lateral groove 22 into said lateral groove 22. In order to provide for the catching force for forcing the valve tissue into the lateral groove 22, that is in order to provide for the reduction of the radial distance D1 between the inner catheter member 8 and the elongate flexible outer member 28, the catching mechanism 32 may be provided by or may comprise the contractability of the elongate flexible outer member 28. That is, the elongate flexible outer member 28 may be provided to be contractible, wherein the elongate flexible outer member 28 may be itself of a substantially non-elastic and non-contractible material, wherein the contracting of the elongate flexible outer member 28 may be achieved by tightening the elongate flexible outer member 28 in a lasso or snare manner. The elongate flexible outer member 28 may also be of a shape-memory material, wherein the elongate flexible outer member 28 may then self-contract when in place around the circumferential valve tissue structure 6 and when certain environmental conditions (for example, temperature conditions are met). In this respect, the elongate flexible outer member 28 may be of nitinol. The elongate flexible outer member 28 may also be of an elastic material, wherein the elongate flexible outer member 28 may be arranged around the circumferential valve tissue structure 6 in an elastically expanded state and may then self-contract by the corresponding elastic restoring forces.

As an alternative to the use of the elongate flexible outer member 28 as providing, or contributing to, the catching mechanism 32 or in addition to the elongate flexible outer member 28 contributing to the formation of the catching mechanism, the catching component 20 may comprise an expandable portion, within which the lateral groove 22 is provided, and which can be radially expanded against the inner side of the elongate flexible outer member 28, whereby the valve tissue is rather pushed into the lateral groove 22 or both pushed and dragged into the lateral groove 22 if both the inner catheter member 8 and the elongate flexible outer member 28 are expanded and contracted, respectively. In this respect, the expandable portion of the catching component 20 may be of a shape-memory material or may be of an elastic material.

To facilitate handling, e.g. during insertion and approach to the tissue, around which the elongate flexible outer member 28 is placed to catch tissue in the lateral groove 22 of the catheter member 8, the elongate flexible outer member 28 may be sheathed in an outer member catheter 29. The outer member catheter 29 may comprise a tubular body and an inner lumen (not shown), through which the elongate flexible outer member 28 may be guided to the heart, for example to the heart valve structure 6, and may be forwarded around the valve tissue structure and then retracted into the outer member catheter 29 to change/reduce a distance D1 between the inner catheter member 8 and the elongate flexible outer member 28. The outer member catheter 29 may be flexible. The outer member catheter 29 may be made from plastic material, such as polymers, or metal or any other material. The outer member catheter 29 may for example be an "active catheter", i.e. a catheter that moves and/or bends actively according to a control signal, actuated for example by shape memory alloy (e.g. nitinol) components heated and/or cooled by electro-thermal converters (e.g. Peltier elements) or actuated by hydraulic actuators. The outer member catheter 29 may also comprise a separate sheath for each end of the snare-shape elongate flexible outer member 28 in the lumen of the outer catheter member 29, whereby all of the sheaths of the outer member catheter 29 may be movable relative to each other and/or relative to the outer catheter member 29 to facilitate positioning of the elongate flexible outer member 28.

Figure 10:
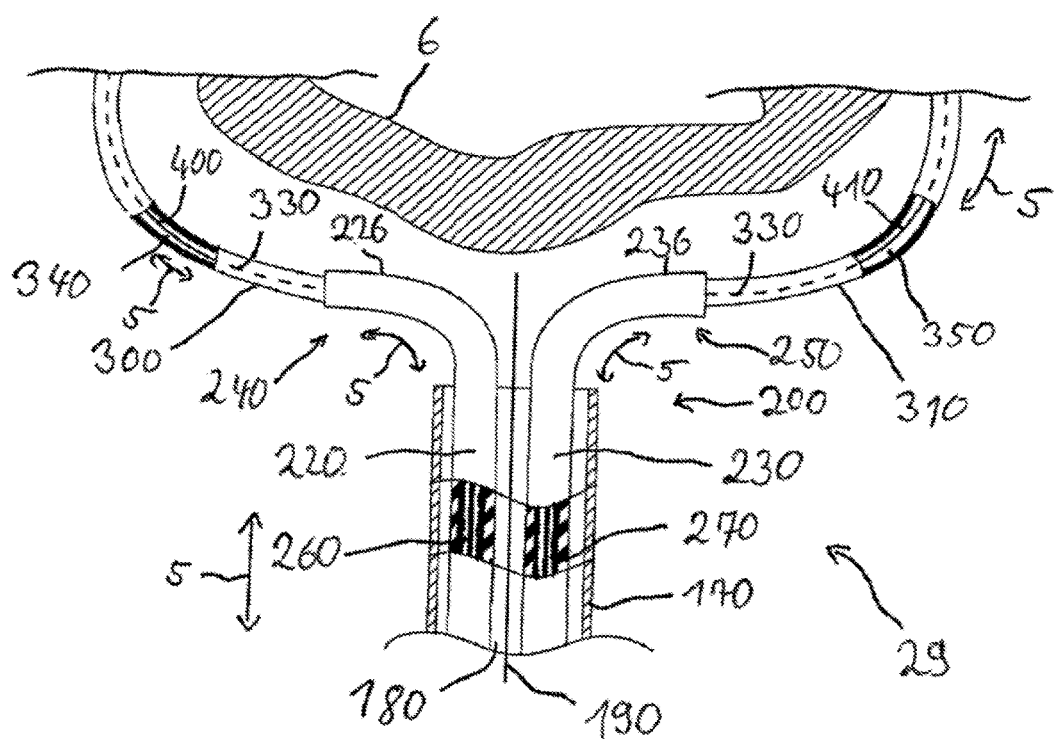
FIGS. 10-12 show an exemplary embodiment of an outer member catheter.

In the following, an exemplary outer member catheter 29 is described in more detail. However, it is to be appreciated that the treatment catheter system 2 may also be used with other outer ember catheters 29 (or without an outer member catheter 29) and is not limited to the embodiments that are described in the following paragraphs. FIG. 10 shows a crossectional view of a distal portion of an exemplary outer member catheter 29 located in the vicinity of the circumferential valve tissue structure 6. FIGS. 11a and 11b show a perspective view of the outer member catheter 29 and FIG. 12 shows how a wire 400 and a catching wire 410 are placed around the circumferential tissue structure 6 of a heart valve 4 that connects a ventricular chamber 4a and an atrial chamber 4b of a human heart in order to provide the elongate flexible outer member 28 extending around the tissue structure 6 from a viewpoint that is located in the atrial chamber 4b. In this respect, elongate flexible outer member 28 may be wire 400 and/or catching wire 410 or a part thereof.

Figure 11:
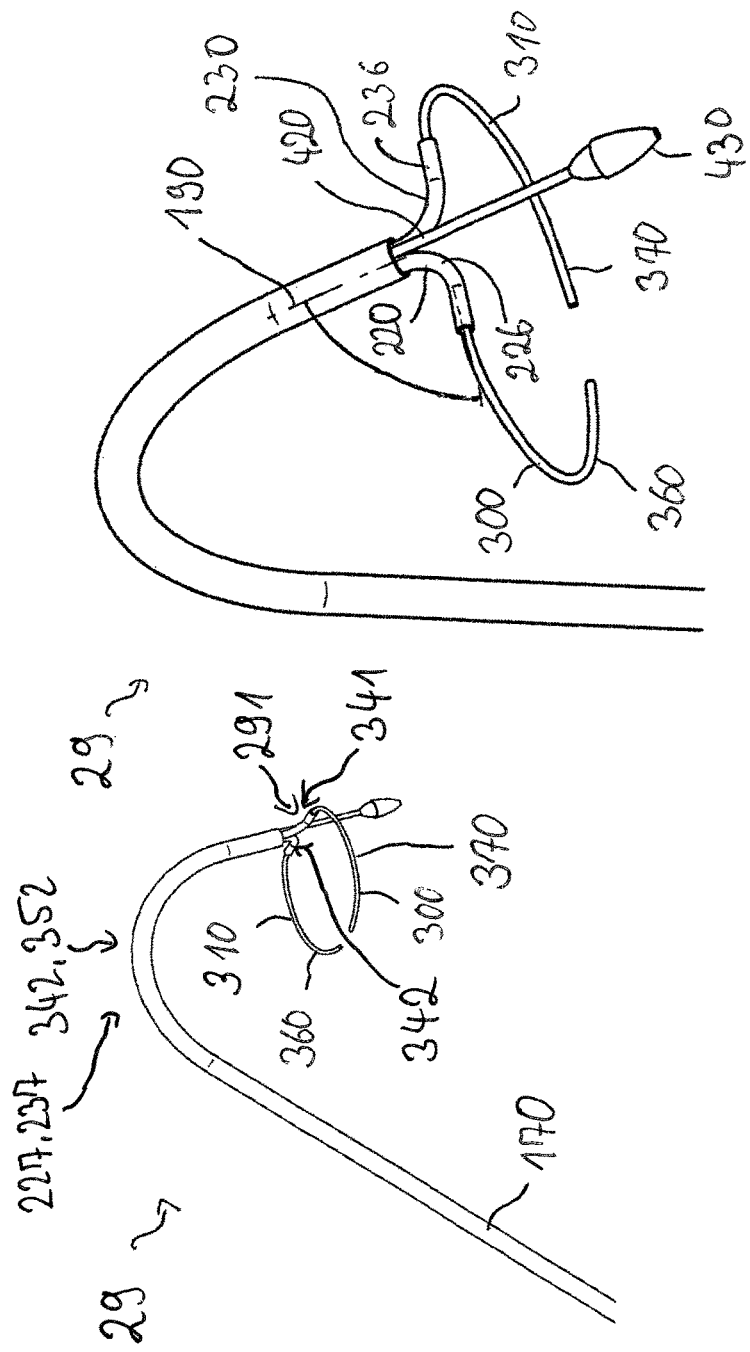
Figure 12:
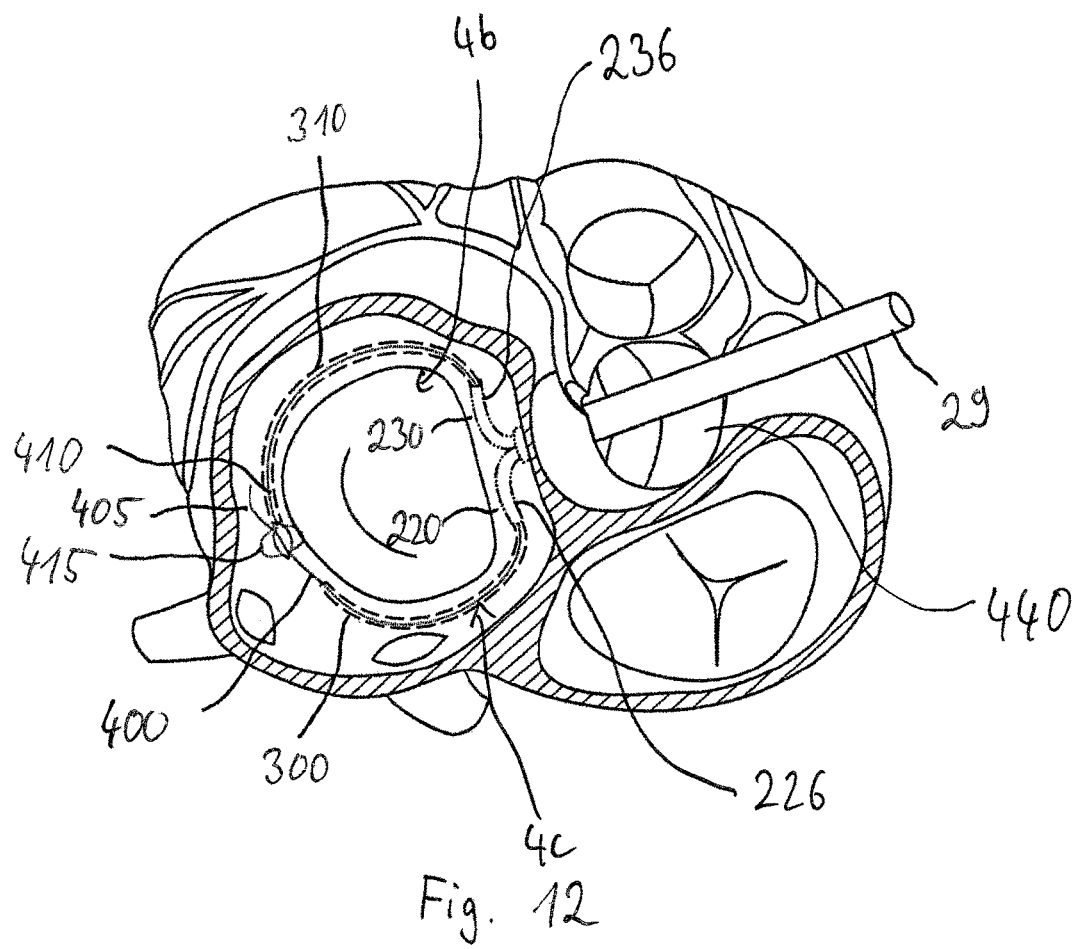

With reference to FIGS. 10 to 12, the outer member catheter 29 may comprise an elongate primary catheter 170 which has an inner lumen 180 and which extends along a longitudinal axis 190 and has a distal end portion 200, first 220 and second 230 elongate secondary catheters each comprising a distal end portion 240, 250 and an inner lumen 260, 270, and each to be disposed in the inner lumen 180 of the elongate primary catheter 170 to be moveable relatively thereto and exposable from the distal end portion 200 thereof, and a first flexing mechanism 291 to provide the distal end portion 240, 250 of the first 220 and/or second 230 secondary catheter with a tendency to assume a first secondary bent shape, wherein the distal end portion 240, 250 of one or both of the first and second secondary catheters 220, 230 is provided to be able to be flexed by the first flexing mechanism 291 to form an arm portion 226, 236 substantially transverse to the direction of the longitudinal axis 190 of the primary catheter 170 to assume the first secondary bent shape, when being exposed from the distal end portion 200 of the elongate primary catheter 170, and wherein the respective arm portion 226, 236 optionally extends at least 4 mm or at least 5 mm or at least 8 mm or at least 10 mm or at least 12 mm in a direction radial to the longitudinal axis 190 of elongate primary catheter 170 with a free end of the respective arm portion facing away from the longitudinal axis 190 so that the respective arm portion 226, 236, with a lateral outer surface thereof, forms a blunt end face extending transversely to the longitudinal axis 190 of the elongate primary catheter 170 and allowing to frontally contact the circumferential valve tissue structure 6 with the outer catheter member 29 in a non-penetrating manner to prevent or reduce trauma or injuries. First 220 and second 230 secondary elongate catheters may each be extending along a longitudinal axis 225, 235, may each also comprise a proximal end portion 280, 290, and may each comprise a secondary alignment portion 227, 237, which may be located between the distal 240, 250 and proximal end portions 280, 290 and adjacent to the distal end portion 240, 250. A second flexing mechanism 292 may provide the secondary alignment portion of the first 220 and/or second 230 secondary catheter with a tendency to assume a second secondary bent shape. The arm portions 226, 236 of the first 220 and second 230 secondary catheters, respectively, may extend in generally opposite directions to each other when the secondary alignment portions 227, 237 of the first 220 and second 230 secondary catheters assume the second secondary bent shape, e.g. in parallel to each other. Optionally, the second secondary bent shape may have a predetermined curvature, for example with a radius of substantially 30 to 70 mm and/or describing an angle of 90° to 270°.

The outer member catheter 29 may further comprise first 300 and second 310 elongate tertiary catheters to be guided by the first 220 and second 230 secondary catheter, respectively, each extending along a longitudinal axis 320, 330 and each comprising a distal end portion 360, 370 and a proximal end portion 380, 390 and each to be moveable relatively to the first 220 and second 230 secondary catheters, respectively, and exposable from the distal end portion 240, 250 thereof.

The first 300 and second 310 tertiary catheters may each have a first 341, 351 and/or a second 342, 352 tertiary alignment portion between the respective distal 360, 370 and proximal 380, 390 end portions thereof, each with a shape-memory structure (e.g. comprising Nitinol or a spring element or the like) providing the first 341, 351 and/or the second 342, 352 tertiary alignment portions with a tendency to assume a first and/or a second tertiary bent shape, respectively, corresponding to the first and/or to the second secondary bent shape, respectively.

The distal end portions 360, 370 of the first 300 and the second 310 tertiary catheters may comprise a shape-memory structure providing them with a tendency to assume a respective bow-shape when being exposed from the distal end portion 240, 250 of the first and second secondary catheters 220, 230, respectively.

The shape-memory structure of the distal end portions 360, 370 of the first 300 and the second 310 tertiary catheters may be such that, when the first 341, 351 and/or the second 342, 352 tertiary alignment portion of the first 300 and the second 310 tertiary catheters are located to mate with the distal end portions and/or the secondary alignment portions 327, 237 of the first and second secondary catheter 220, 230, assuming their respective first and/or second bent shape, respectively, the distal end portions 360, 370 of the first 200 and the second 310 tertiary catheters are provided with a tendency to assume bow-shapes extending oppositely towards to each other to form a loop-shape.

Further, the first 341, 351 and/or the second 342, 352 tertiary alignment portion of the first 300 and the second 310 tertiary catheters of the outer member catheter 29 may be located to mate with the distal end portions 240, 250 and/or the secondary alignment portions 227, 237 of the first and second secondary catheter 220, 230, assuming their respective first and/or second bent shape, respectively, the distal end portions 360, 370 of the first 300 and the second 310 tertiary catheters are fully operatively exposed from the distal end portions 240, 250 of the first 220 and second 230 secondary catheters.

The first and second distal end portions 360, 370 of the first 300 and second 310 tertiary catheter are exposed from the distal end portion 240, 250 of the first 220 and second 230 secondary catheters, the distal end portions 360, 370 of the first 300 and second 310 tertiary catheters each substantially extend in a substantially same plane that is transversal to the longitudinal axis 190 of the primary catheter 170 of the outer member catheter 29.

The first 300 and second 310 tertiary catheters of the outer member catheter 29 each may comprise an inner lumen 340, 350, wherein a wire 400 having a free distal end 405 is provided in the inner lumen 340 of the first tertiary catheter 300 and a catching wire 410 with a catching component 415 on a distal end thereof may be provided in the inner lumen 350 of the second tertiary catheter 310, and wherein both the wire 400 and the catching wire 410 are provided to be movable relative to their respective tertiary catheter 300, 310 and exposable from and retractable into a distal end portion 360, 370 thereof, so that the free distal end 405 of the wire 400 can be caught with the catching component 415 to form a loop around the circumferential tissue structure 6 that may serve as and/or be the flexible outer member 28 as described herein.

The catching component 415 may be a catching basket and/or a lasso and/or a snare.

The curvature of the second secondary bent shape may mate to the curvature of an aortic arch 440 of a mammal heart and the circumferential tissue structure 6 is part or all of the mitral valve apparatus.

The curvature of the second secondary bent shape may mate to the curvature of a connection channel from the superior vena cava to the pulmonary artery of a mammal heart and the circumferential tissue structure 6 may be part or all of the tricuspid valve apparatus of a mammal (e.g. human) heart.

The elongate primary catheter 170 of the outer member catheter 29 may further comprise a front body tube 420 moveably disposed in its inner lumen 180, wherein the front body tube 420 may comprise a blunt front body 430 on its distal end portion that is configured to selectively open and close the distal end portion 200 of the elongate primary catheter 170 by movement of the front body tube 420 in a distal or proximal direction, respectively, of the elongate primary catheter 170 of the outer member catheter 29.

One or both of the first 300 and second 310 tertiary catheters may be received in the inner lumen 260, 270 of the first 220 and second 230 secondary catheter of the outer member catheter 29, respectively, to be guided by them.

The first 300 and/or second 310 tertiary catheter may comprise an inner lumen 340, 350, wherein one or both of the first 220 and second 230 secondary catheter, respectively, may be received in the inner lumen 340, 350 of the first 300 and/or second 310 tertiary catheter, respectively, so that the first 300 and/or second 310 tertiary catheter may be guided by the first 220 and second 230 catheter, respectively. While in the above paragraphs an exemplary outer member 29 is described, other outer member catheters 29 that may at least partially or fully surround the circumferential valve tissue structure 6 may be utilized with the invention. It must also be appreciated that no outer member catheter 29 may be necessary at all if outer member 28 is placed at least partially or fully around the valve tissue structure 6 (e.g. an outside thereof) in another way or by another means.

Arrows 5 in FIG. 10 schematically indicate possible directions for reversible kinematic movement of components of the outer member catheter 29.

In the following, the catheter member 8 and the catching component 20 are described in more detail. The catching component 20 may be separate from the catheter member 8 and may be provided to be insertable into the inner lumen 14 from the proximal end portion 18 of the catheter member 8 and may be forwardable through the inner lumen 14 to the distal end portion 16 to be exposed to the outside of the catheter member 8 at said proximal end portion 18. Correspondingly, the catching component 20 may then be retracted through the inner lumen 14 of the catheter member 8 and may be removed from the catheter member 8 at the distal end portion 16 thereof. However, when placed at the distal end portion 16 of the catheter member 8, the catching component 20 cannot be removed from the catheter member 8 in order to ensure that the catching component 20 will not accidentally remain within the interior of the valve tissue structure 6 when retracting the catheter member 8 therefrom.

The catching component 20 may also be integrally formed with the catheter member 8 at the distal end portion 16 of the catheter member 8 or fixedly attached to the catheter member 8 at the distal end portion 16 thereof to provide a stationary catching component 20, that is stationary and non-moveably with respect to the catheter member 8. In this respect, the catching component 20 may be formed by a tip body providing a tip end portion of the catheter member 8 at the distal end portion 16 thereof.

Figure 4:
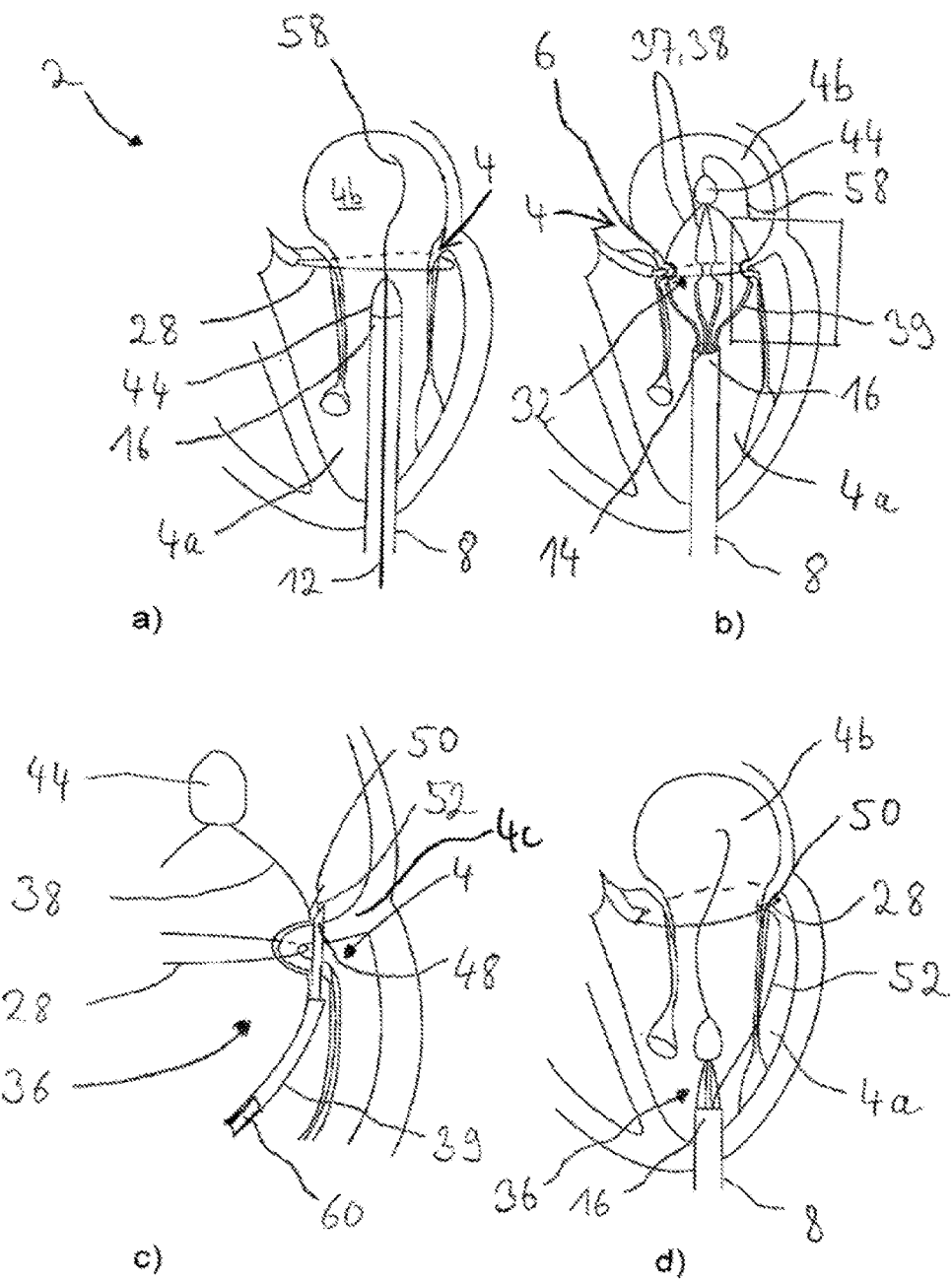
FIGS. 4a to 4d schematically show a treatment catheter system according to embodiments.

The catching component 20 may be generally made of a solid body, in which a lateral transverse recess is formed to provide the lateral groove 22. The catching component 20, however, may also be formed by a grid-type or mesh-type cage body 36 (cf. for example FIG. 4b) comprising grid elements 37 or mesh elements, respectively, wherein the grid elements 37 may be formed by respective elongate wires 38 which are forwardable through the inner lumen 14 of the catheter member 8 (cf. for example embodiment of FIGS. 4a-4d, 5 and 6). The wires 38 themselves may be arranged within elongate flexible sheaths 39 and may be moveable relative to their respective sheath 39 to be forwardable and retractable therethrough. The catching component 20, for example, the wires 38 thereof, may be made from steel (e.g. comprising iron, chromium and carbon), from nickel, from alloys substantially comprising nickel (e.g. nichrome, e.g. nitinol), from polymer (e.g. PVC, PP, PS, polyamide or aromatic polyaramides), from titanium, from alloys substantially comprising titanium (e.g. Ti 6Al 4V), from platinum, from gold, from aluminium or from alloys substantially comprising aluminium. The catching component 20 may be made from other materials as well. The catching component 20 may be made by casting techniques. The catching component may be made by metal-cutting manufacturing techniques.

The grid-type or mesh-type cage body 36 may be retractable into the inner lumen 14 of the catheter member 8. Forwarding and/or retracting of the wire body 36 (e.g. basket) may be actuated manually, or by an electric motor.

The cage body 36 may have a reinforcing liner 40 (cf. for example FIG. 6) of tubular shape and which may be arranged circumferentially at the inner circumferential side of the cage body 36 or at the outer circumferential side of the cage body 36. The liner 40 may be made from the same material as the cage body 36. The liner 40 may also be made from a different material than the cage body 36. The liner 40 may be made from steel (e.g. comprising iron, chromium and carbon), from nickel, from alloys substantially comprising nickel (e.g. nichrome, e.g. nitinol), from polymer (e.g. PVC, PP, PS, polyamide or aromatic polyaramides), from titanium, from alloys substantially comprising titanium (e.g. Ti 6Al 4V), from platinum, from gold, from aluminium or from alloys substantially comprising aluminium. The liner 40 also may be made from other materials.

The liner 40 may be joined to the cage 36 by gluing, soldering, welding or other means. The liner 40 may also be elastic and may be inserted within the cage body 36 to be elastically clamped against the circumferential inner side of the cage body 36 or may be arranged around the cage body 36 to be elastically clamped against the circumferential outer side of the cage body 36.

The liner 40 may be of a mesh-type body 40 having a mesh size D2, or a sheet of foil material comprising holes therein. The mesh size D2 of the liner 40 may be smaller than a mesh-size of a mesh-type cage body 36 or than a circumferential distance of grid elements of a grid-type cage body 36. For example, the mesh size D2 may be equal or less than 50%, 30% or 20% of the mesh size of a mesh-type cage body 36 or of the circumferential distance of grid elements of a grid shape cage body 36. The liner 40 may be a foil-material substantially not comprising holes.

The cage body 36 may be placed and/or located in the interior 10 of circumferential tissue structure 6 so that the lateral groove 22 is located on the side of the ventricular chamber 4a of the annulus 4c of a natural valve 4, e.g. having a distance from the natural valve annulus 4c, i.e. the lateral groove 22 may be placed to be a sub-annular lateral groove 22.

The catching component 20 may comprise a temporary artificial heart valve 42. The temporary artificial heart valve 42 may be fixedly attached to the catching component 20, for example fixedly attached to the cage body 36. The temporary artificial heart valve 42 may be attached to the liner 40. The temporary artificial valve 42 may be radially compressible. The temporary artificial valve 42 may be radially expandable. The temporary artificial valve 42 may be compressed when in the inner lumen 14 of the catheter member 8. The temporary artificial valve 42 may be expanded when forwarded from the inner lumen 14 of the catheter member 8 to the outside thereof. The temporary artificial valve 42 may be provided to enable a prolonged operation procedure without the risk of creating valve insufficiency.

The grid-type or mesh-type cage-body 36 as part of the catching component 20 and part of the catching mechanism 32, allows to safely clamp circumferential valve tissue 6 between the cage body 36 and the outer member 20, wherein nevertheless a blood flow is allowed between for example, ventricular chamber 4a and atrial chamber 4b through the gaps between the grid elements and/or mesh elements, wherein the mesh type liner 40 does not substantially limit blood flow. Accordingly, a treatment of the heart can be carried out on the beating heart, wherein a slight back flow during the contraction period of the heart may be accepted, which slight back flow may be further reduced or even prevented when using the above described temporary artificial valve 42. The device shown in FIG. 2 may allow only small blood through flow so that treatment time may be correspondingly reduced.

The cage body 36 may be terminated by a substantially non-compressible front body 44, e.g. a distal end portion plug 44. The front body 44 may have a rounded outer side. The front body 44 may have a blunt front nose. The front body 44 may have an outer diameter slightly larger than an inner cross-sectional diameter of the inner lumen 14 of the distal end portion 16 of the catheter member 8 to be able to provide a plug for closing a frontal end opening of the inner lumen 14 of the catheter member 8.

The front body 44 may be connected to some or all of the wires 38 forming the cage body 36 in order to bias or prestress the cage body 36. The front body 44 may be attached to some or all of the wires 38 forming the cage body 36 in order to combine them at the longitudinal axis 12 of the catheter member 8, wherein the front body may be correspondingly arranged coaxially to the longitudinal axis 12 of the catheter member 8. The cage body 36, that is, for example, the wires 38 and/or the grid- or mesh-type body thereof, may converge its/their front end, and may correspondingly converge towards the front body 44.

The non-compressible front body 44 may serve several functions: to seal the inner lumen 14 of the catheter member 8 when the catching component 20 is retracted into the inner lumen 14 of the catheter member 8 and/or to facilitate atraumatic insertion and positioning of the catheter member 8 by providing a conical tip.

The lateral groove 22 may extend continuously or in an interrupted manner around the whole circumferential perimeter of the catching component 20 traverse to the longitudinal axis 12. The lateral groove 22 may be formed around only a partial circumferential perimeter, e.g. forming an arc of a circle equal or less than 30, 45, 90, 180, or 270 degrees. The lateral groove 22 may also be formed by the transversely (transverse to longitudinal axis 12) extending recesses (cf. FIG. 2).

Figure 6:
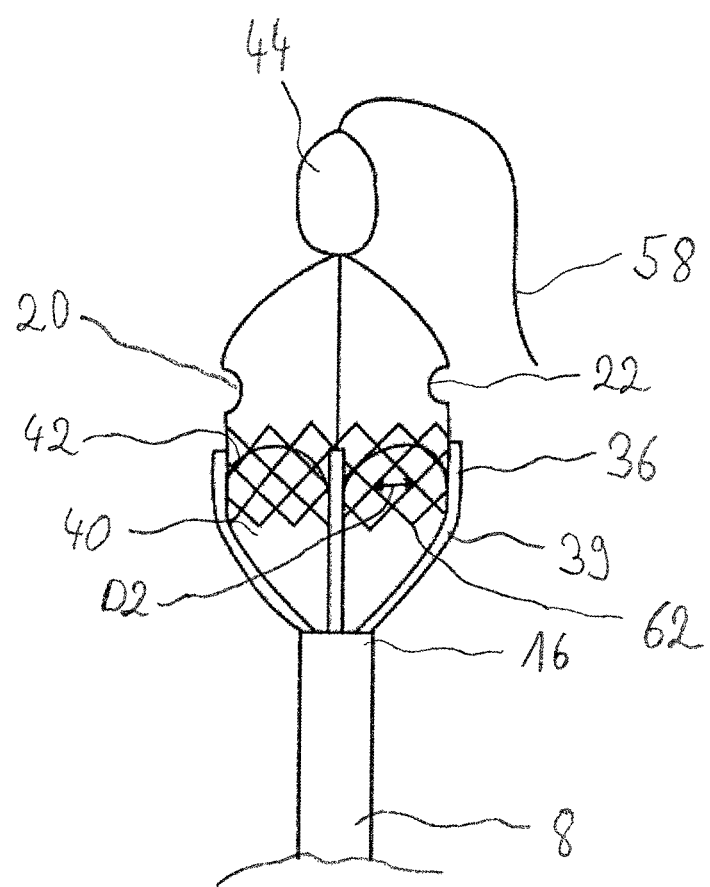
FIG. 6 schematically shows an embodiment of a catheter member of a treatment catheter system according to an embodiment.

The lateral groove 22 may be provided on the cage body 36 of the catching component 20 in a manner to be provided on each wire 38 or on one wire or a on plurality of wires or on each but one wire forming the cage body 36 so that each groove 22 extends transverse to the longitudinal axis 12 of the catheter member 8 (cf. for example FIGS. 4b and 6).

The lateral groove 22 on the cage body 36 may be provided by radially and inwardly bent portions of each or of some of the wires 38 forming the cage 36, i.e. the groove 22 may be provided without removing material but by bending (cf. for example FIGS. 4b and 6), wherein the bent portions are provided at substantially the same level along the longitudinal axis 12.

Wires 38 or arms 38 forming the cage body 36 may be arranged to have the same angular or circumferential distance from each other. Wires or arms 38 forming the cage body 36 may be arranged to have different angular or circumferential distances between each wire 38.

Wires 38 forming the cage body 36 may be arranged to form a substantial round (transverse to the longitudinal axis 12) cage body 36 that is coaxially positioned and aligned with the longitudinal axis 12 of the catheter member 8, at least when the cage body 36 is extended on the distal end portion 16 of the catheter member 8. Wires 38 forming the cage body 36 may be arranged to form a substantially triangular-shaped or rectangular-shaped or pentagonal-shaped or hexagonal-shaped or dodecagonal-shaped or other polygonal-shaped cage body 36 that is coaxially positioned and aligned with a longitudinal axis 12 of the catheter member 8, at least when the cage body 36 is extended on a distal end portion 16 of the catheter member 8. The cage body 36 may also be arranged to be not coaxially aligned with the longitudinal axis 12 of the catheter member 8, e.g. excentrically aligned with the longitudinal axis 12 of the catheter member 8.

Figure 13:
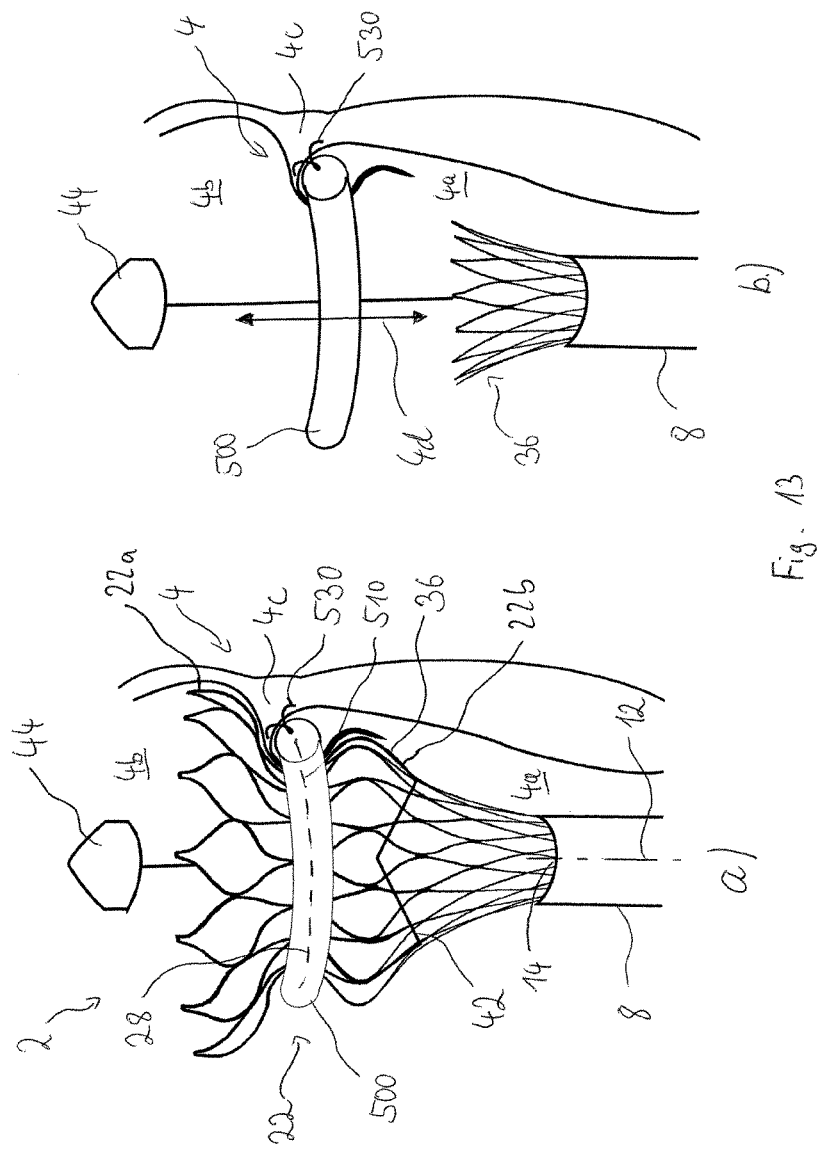
FIGS. 13a and 13b show a view of a catheter member of a treatment catheter system and a prosthesis according to an embodiment.

As shown e.g. in FIG. 13*a*, the lateral groove 22 may define a distal cage section 22*a* that may be the part of the catching component 20 (e.g. when it is formed as cage body 36) that is located on a distal side of the lateral groove 22 (along the longitudinal axis 12) and a proximal cage section 22*b* that may be the part of catching component 20 (e.g. cage body 36) that is located on a proximal side of the lateral groove 22 (along the longitudinal axis 12). The cage body 36 and/or the catching component 20 may have a curvature or bent shape, that, when seen in a direction perpendicular to the longitudinal axis 12, changes the curvature from a concave curvature of the lateral groove 22 to a convex curvature at the transition between the lateral groove 22 and the distal cage section 22*a* and/or the proximal cage section 22*b*, as it is show, e.g. in FIGS. 13*a* and 13*b*.

In this respect, the catching component 20/cage body 36 may have a diameter at an axial level (with respect e.g. to longitudinal axis 12) of the lateral groove 22 that is smaller than a diameter of a natural valve annulus 4*c*. The catching component 20/cage body 36 may have a diameter at an axial level (with respect e.g. to longitudinal axis 12) adjacent to the catheter member 8 that approaches the crossectional diameter of the catheter member 8 and is smaller than a diameter of a natural valve annulus 4*c*.

With reference to e.g. FIGS. 13*a* and *b*, diameters and/or axial lengths of the catching component 20 (e.g. cage body 36) may be configured so that distal cage section 22*a* may be located/placed at least partially (e.g. substantially) in an atrial chamber 4*b* and that proximal cage section 22*b* may be located/placed at least partially (e.g. substantially) in the interior 10 of the circumferential valve tissue structure 6 with the lateral groove 22 being located on a ventricular side (that is the side of the ventricular chamber 4*a*) of the natural valve annulus 4*c* while having a (small) distance to said annulus 4*c*, e.g. at least when the cage body 36 is forwarded from catheter member 8.

A diameter of the catching component 20 (e.g. of the cage body 36) may have a radial diameter (with respect to longitudinal axis 12) in its distal cage section 22*a* that is larger than a radial diameter in its proximal cage section 22*b*, at least when the cage body 36 is forwarded form the inner lumen 14 of catheter member 8 and is fully expanded. A longitudinal extension length (with respect to longitudinal axis 12) of the distal cage section 22*a* may be shorter than a longitudinal length of the proximal cage section 22*b*. A radial diameter (with respect to the longitudinal axis 12) of catheter member 8 may be smaller than a diameter of catching component 20 (e.g. cage body 36), at least when the catching component 20 is forwarded from the catheter member 8. With respect to longitudinal axis 12, a radial diameter of the distal cage section 22*a* may increase in distal direction along longitudinal axis 12 starting from lateral groove 22 to a maximum diameter and then may decrease again so that the distal cage section 22*a* may form a convex profile (c.f FIG. 13*a*, however embodiments may comprise an even more distinctive convex profile). The proximal cage section 22*b* may form a convex profile with increasing and then decreasing radial diameters (with respect to longitudinal axis 12) from a bottom of lateral groove 22 longitudinally along catching component 20 in a proximal direction along longitudinal axis 12.

The catheter member 8 may be a hollow tubular body, wherein the inner lumen 14 or additional lumens may have such a cross-sectional diameter that one re treatment tools for treating the caught valve tissue 6 or valve tissue adjacent to the caught valve tissue can be simultaneously arranged therein and are movable relative therethrough. Such treatment tools may include a perforation component 48 for perforating the valve tissue 6, or drug supplying tools allowing supply of a drug, such as, for example, anticalcification drugs, drugs against tissue proliferation, drugs against thrombus formation or for platelet activation, to the valve tissue 6 to be treated.

The catching component 20 may be movable relative to the catheter member 8. The catching component 20 may be configured to be forwarded and retracted relative to the catheter member 8 according to a control-command. The catching component 20 may be fully sheathed in a lumen 14 of the catheter member 8 when fully retracted. The catching component 20 may be integrally formed with the catheter member 8 at the distal end portion 16.

The catching component 20 may comprise a conical and/or blunt front part and may be arranged on the catheter member 8 so as to be exposed at the distal end portion 16 of the catheter member 8, thereby being configured to cause least tissue damage when the catheter member 8 is inserted and forwarded to the tissue to be treated.

The perforation component 48 may comprise or may be a needle, a hollow needle or another tubular body 48 comprising an inner lumen 54 and having a sharpened or peaked end. The perforation component 48 may be provided such that it can be forwarded and retracted through one, some or all of the wire sheaths 39 of the wires 38 forming the cage body 36 (cf. for example FIG. 4*d*) in order to perforate tissue. The perforation component 48 may be provided in the inner lumen 14 or any additional lumen of the catheter member 8, for example in parallel and separate from the sheaths 39 and wires 38 such as to perforate tissue 6 that is caught in a lateral groove 22 of the catching component 20. The perforation component 48 may be configured to carry an anchor component 50 to perforate the caught tissue with said anchor component 50 which then remains at the tissue when the catheter member 8 is retracted. The anchor 50 may be placed on a tip of the perforation component 48. A chord, for example an artificial chord, for example of ePTFE, nylon or Kevlar, 52 may be fixedly attached to the anchor 50. The chord 52 may be used to replace a ruptured native chord of for example a mitral or tricuspid valve. The anchor 50 may be configured to allow joining of adjacent layers of tissue together, e.g. to join two, three or four layers of tissue or a plurality of layers of tissue together. In this regard, a so-called edge-to-edge mitral valve repair (Alfieri stitch) may be carried out by having, for example, half of the circumferential mitral valve tissue caught in the lateral groove 22 and having oppositely arrange tissue parts perforated by the anchor 50 on the perforation component 48 (cf. for example FIGS. 7-8). The chord 52 may be positioned in an inner lumen 54 of the perforation tool 48. The perforation component 48 may be designed so that the anchor 50, after it is fixated to tissue or adjacent layers of tissue, remains fixated to the tissue when the catheter member 8 is retracted. Thereby tissue may remain joint together after the perforation component 48 has been retracted. Similarly, a chord 52 may remain attached to the anchor 50 which is in turn fixated to tissue and/or joining together tissue after the catheter member 8 has been retracted.

The perforation component 48 may be provided with a needle, e.g. a hollow needle. The needle may be used to deliver drugs and/or substances to tissue.

The perforation component 48 may be flexible and/or the needle may flexible. The perforation component 48 may be rigid and/or the needle may rigid or may have a rigid end portion.

The perforation component 48 may also be a separate part outside of the catheter member 8 and may be sheathed by a separate sheath (not shown), within which it is moveably received. The perforation component 48 may be forwarded through the catheter member 8 through the inner lumen 14 of the catheter member 8 and/or through the sheath 39 of a wire 38 forming the cage body 36 of the catching component 20.

According to FIG. 1, the catheter member 8 and the elongate flexible outer member 28 are positioned relative to each other such that the elongate flexible outer member 28 and the lateral groove 22 are arranged in a manner that valve tissue 6 is forced, for example dragged, into the lateral groove 22 via the catching opening 26 by the elongate flexible outer member 28 when a radial distance D1 (cf. for example FIG. 2) between the elongate flexible outer member 28 and the catheter member 8 is reduced. This results in the valve tissue structure 6 being immobilized in the lateral groove 22 by being caught in the lateral groove 22 and retained therein by the elongate flexible outer member 28 (see also e.g. FIGS. 2 and 3). The immobilization of the valve tissue or otherwise heart tissue allows safe treatment of said immobilized tissue, for example, for carrying out heart valve reconstruction or heart valve 4 replacement by a valve prosthesis.

The radial distance D1 between the elongate flexible outer member 28 and catheter member 8 is reduced by a catching mechanism 32, which is operable by an interventional cardiologist or a surgeon or any other person. In all embodiments, the catching mechanism 32 may include a lasso or snare formed by the flexible outer member 28 to allow the operator to contract the snare and to thereby reduce the radial distance D1 between the elongate flexible outer member 28 and the catheter member 8 (cf. FIGS. 1, 4a, 4b and 4d). In some embodiments, the catching mechanism 32 may be actuated e.g. by a servo motor or directly by the hands of the operator.

Figure 2:
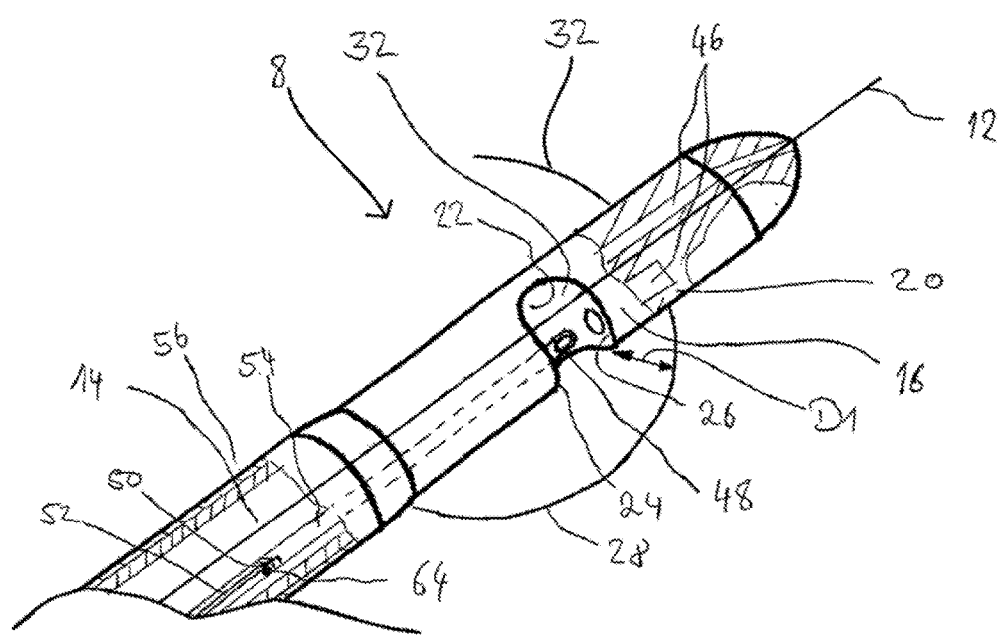
FIG. 2 shows a partially cut perspective view of a catheter member of a treatment catheter system according to an embodiment.

FIG. 2 shows a more detailed, partially cut perspective view of a catheter member 8 according to an embodiment, which may be used as catheter member in the embodiment of FIG. 1. Generally, the catheter member 8 is of an elongated, tubular design. In some embodiments, the catheter member 8 may comprise different radii, diameters and/or bevels to facilitate insertion in the heart and approach to a heart valve 4.

The catching component 20 at the distal end portion 16 of the catheter member 8 comprises a lateral groove 22 that extends transverse of the longitudinal axis 12 of the catheter member 8. The lateral groove 22 provides a catching opening 26 on a circumferential outer side 24 of the catching component 20. Via the catching opening 26, heart valve tissue 6 can be caught in the lateral groove 22 by interaction of the catching component 20 with the flexible outer member 28 (not shown in FIG. 2) so that valve tissue 6 is immobilized between the flexible outer member 28 and the lateral groove 22. According to FIG. 2, the catching component 20 is formed as a tubular member which longitudinally extends through the catheter member 8 and is moveable relative to the catheter member 8 in the longitudinal direction thereof and/or rotationally. Thereby, the catching component 20 itself defines an inner lumen coincident with the inner lumen 14 of the catheter member 8, and through which the operation tools are guided towards the distal end portion 16. The catching component 20 of FIG. 2 may also be integrally formed at the distal end portion 16 of the catheter member 8. Further, the catching component 20 may include longitudinal inner channels 46 respectively assigned to operation or treatment tools such as the perforation component 48 which may be guided therein. The catheter member 8 may also be a flexible solid body having longitudinal guiding channels defining the inner lumen 14 as a plurality of separate lumens and guiding the operation or treatment tools to the distal end portion 16, where they may be aligned with the afore-discussed inner channels 46 in the catching component 20.

In this embodiment, the catching component 20 is also equipped with an elongate perforation tool 48, e.g. a needle or hollow needle 48, to perforate or puncture the caught valve tissue or adjacent valve tissue in order, for example, to attach an anchor 50 with a chord 52 (see e.g. FIG. 4c for an illustrative embodiment of anchor 50 and chord 52) to the valve tissue 6 or tissue adjacent to the valve 4. For this, an anchor 50 with or without an attached chord 52 may be guided through the inner lumen 64 of the hollow needle 48 into the lateral groove 22.

The hollow needle 48 loaded with anchor 50 and/or chord 52 is contained in the inner lumen 14 of the catheter member 8 and can be controlled by an interventional cardiologist or a surgeon or another person to move it forward towards the distal end portion 16 and en route perforate valve tissue caught in the lateral groove 22. Afterwards, the hollow needle 48 can similarly be controlled to fully retract backwards towards the proximal end portion 18 so that it is fully sheathed by the catheter member 8. The anchor 50 can be forwarded through the hollow needle 48 and be exposed at the distal end thereof to thereby enter into the perforation created by the needle. The anchor 50 may then remain seated in the valve tissue with the chord 52 extending through the valve tissue.

In FIG. 2, the hollow needle 48 is shown for in an intermediate position with its tip extending into the lateral groove 22.

In other embodiments, (instead of an anchor) drugs or other substances (e.g. to improve medical imaging) and/or devices for treatment or interaction can be applied to the caught valve tissue by the hollow needle 48 in the catching component 20. In some embodiments, the hollow needle 48 can be exchangeable so that an optimal needle can be chosen to e.g. attach an anchor 50 to the valve tissue 6 or deliver drugs or so that the hollow needle 48 can be replaced once the tip of the needle is worn after use. In some embodiments, the elongate perforation component 48 (e.g. the hollow needle 48) may be flexible so that it may be guided laterally out of the lateral groove to penetrate laterally located tissue to, for example, forward a drug thereto.

In the embodiment shown in FIG. 2, the catching component 20 is moveable relative to the catheter member 8 and can be forwarded or retracted via the inner lumen 14 of the catheter member 8 to cause least collateral damage to tissue during insertion of the catheter member 8. In other embodiments, the catching member 20 is integrally formed with the catheter member 8 at the distal end portion 16 of the catheter member 8. FIG. 2 illustrates the catching component 20 in a position, where it is forwarded from the inner lumen 14 of the catheter member 8 and (apart from the for illustrative purposes not fully retraced needle 48) is ready to interact with the elongate flexible outer member 28 in order to drag valve tissue 6 in the lateral groove 22.

The catheter member 8 may be made flexible to be bendable along its longitudinal direction.

In FIG. 2, the distal end portion 16 of the catheter member 8 is shown with a conical and round distal end portion 16, whereas the distal end portion 16 may also be blunt.

Figure 3:
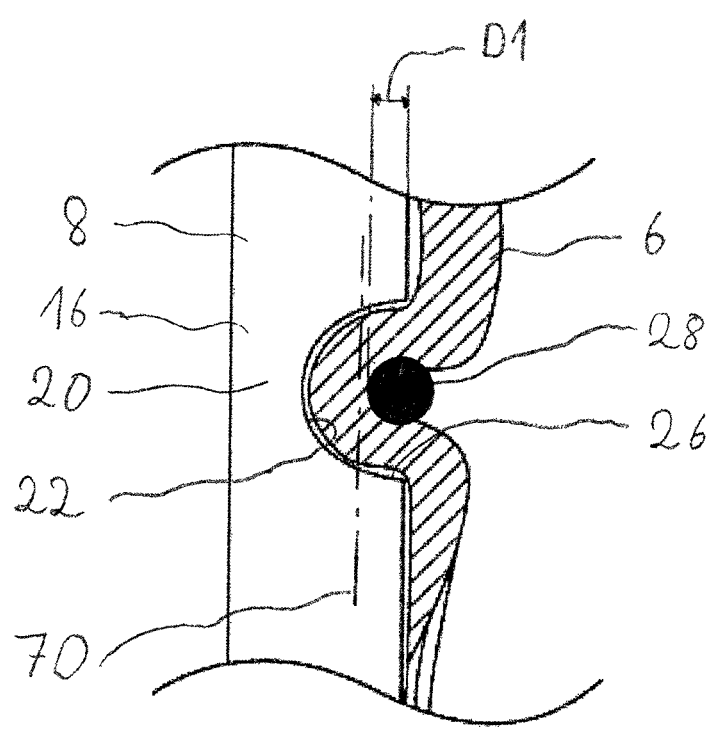
FIG. 3 shows schematically the interaction of an outer member and a catheter member of a treatment catheter system according to an embodiment.

FIG. 3 shows schematically the interaction of the elongate flexible outer member 28 and the catheter member 8 of a treatment catheter system 2 to immobilize tissue 6 of a valve 4 according to one embodiment. In FIG. 3, the radial distance D1 between the elongate flexible outer member 28 and catheter member 8 has been reduced to catch tissue 6 of the valve 4 in the lateral groove 22 located at the distal end portion 16 of the catheter member 8 via the catching opening 26. In FIG. 3, the path along which the flexible perforation component 48 can be forwarded and retracted in order to perforate the valve tissue 6 according to one embodiment indicated by a dashed line 70.

The lateral groove 22 may be designed to have different geometric dimensions. The larger the lateral groove 22 is, the more tissue of the circumferential tissue structure 6 can be caught in the lateral groove 22, thereby the length of leaflet tissue along the surface of lateral groove 22 may be increased, thereby the perforation component 48 may perforate the leaflet tissue in two areas. In this case, an anchor 50 may be designed to be positioned to fixate the two perforated positions together. The anchor 50 may be fixated in each of the two perforated positions. This is creating locally a shrinkage or shortening of the leaflet length (e.g. the circumferential tissue structure 6) in an axial direction of the circumferential tissue structure 6. This may be done at several locations of the tissue structure 6 (e.g. by using one or more arms 38 of the wire body 36, each comprising a lateral groove 22) so that a uniform shortening of the leaflet may be obtained. The inner basket (e.g. wire body 36) may also comprise a tissue that can be stapled on the native leaflet (e.g. to the circumferential tissue structure 6).]

FIG. 4a and FIG. 4b show a treatment catheter system 2 according to another embodiment. With reference to FIGS. 4a and 4b, the elongate flexible outer member 28 and the catheter member 8 are disposed around tissue 6 of a heart valve 4, in this case again the mitral valve 4, however elongate flexible outer member 28 and catheter member 8 can be arranged to interact with other heart valves such as the tricuspid valve, the pulmonic valve, or the aortic valve.

The distal end portion 16 of catheter member 8 is shown positioned in such a way that it is ready for interaction with the elongate flexible outer member 28. In this embodiment, the catching component 20 of the catheter member 8 contains an extendable and retractable cage body 36, formed by elongate wires 38 which exit the catheter member 8 at the distal end thereof and which are circumferentially spaced to define as grid elements the cage body 36. The wires 38 are connected to each other at their distal ends.

The catching component 20 can be extended from the inner lumen 14 and/or retracted into the inner lumen 14 of the distal end portion 16 of the catheter member 8.

In FIG. 4a, the wires 38 forming the cage body 36 are in a position where they are retracted in the lumen 14 of the distal end portion 16. In some embodiments, the wires 38 are strained and/or compressed to contain elastic energy when being retracted in the lumen 14 of the distal end portion 16, so that they radially self-expand when being moved out of the inner lumen 14 of the catheter member 8.

According to FIGS. 4a and 4b, the distal end portion 16 is terminated by a substantially non-compressible front body 44, e.g. a distal end portion plug 44, having a rounded outer side (here, the front body is of ellipsoid shape) and having an outer diameter slightly larger than an inner cross-sectional diameter of the lumen 14 of the distal end portion 16 of the catheter member 8 to be able to provide a plug for closing a frontal end opening of the inner lumen 14 of the catheter member 8. A front wire or string 58 may be provided to help guiding the catheter member 8 to the final position in the heart. The end portion plug 44 of the distal end portion 16 can be conical as shown in FIGS. 4a and 4b to facilitate positioning the catheter member 8 in the heart and/or other human or animal organs, wherein the plug 44 may have a blunt front end or nose.

In some embodiments, the front body 44 is connected to some or all of the wires 38 forming the cage 36 in order to radially confine the cage 36 at the distal end thereof.

In some embodiments, the non-compressible front body 44 can serve several functions: to seal the inner lumen 14 of the catheter member 8 when the catching component 20 is retracted into the inner lumen 14 of the catheter member 8 and/or to facilitate atraumatic insertion and positioning of the catheter member 8 by providing a conical tip.

In FIG. 4b, the treatment catheter system 2 is shown with the catching component 20 extended from the distal end portion 16 of the catheter member 8. The wire cage body 36 is radially expanded by elastic energy stored in the strained/compressed wires 38. The radial expansion of the wire cage body 36 may also be achieved by an auxiliary expansion device, such as a radially expandable (for example via inflation) balloon arranged within the cage body 36 and expandable in a controlled manner.

In FIG. 4a or 4b, the catching mechanism 32 is formed by the radially contractible loop design of the elongate flexible outer member 28 in combination with the radially expandable cage body 36 and the lateral groove 22 defined by the wires 38 of the cage body 36. The catching mechanism 32 can be operated by an interventional cardiologist or a surgeon to reduce the radial distance or gap D1 between the elongate flexible outer member 28 and catheter member 8 so that tissue 6 of the mitral valve 4 gets caught and immobilized in the lateral groove 22 between the elongate flexible outer member 28 and the inner catheter member 8.

When the tissue of the valve 4 is caught and immobilized as described above with reference to FIGS. 4a and 4b, interaction and/or treatment with the tissue, for example valve repair or reconstruction, can be safely and reliably carried out.

FIG. 4c and FIG. 4d show an embodiment of the treatment catheter system 2 that is similarly designed as the embodiment described with reference to FIG. 4a and FIG. 4b and which also allows interaction, e.g. fixating an anchor 50 with or without a chord 52 or the delivery of substances or drugs to the tissue of the valve 4 or adjacent tissue via a perforation component 48.

FIG. 4c shows an enlarged view of the area indicated by a frame in FIG. 4b. In this embodiment of the treatment catheter system 2, the wires 38 that form the cage body 36 are arranged in hollow tubular sheaths 39 which comprise a respective inner lumen 60. When tissue of the valve 4 is caught in the lateral groove 22 by the elongate flexible outer member 28 and thereby gets immobilized, the elongate flexible perforation tool 48, e.g. the flexible needle 48 may be extended from the lumen 60 of one or a plurality of the sheaths 39. The flexible perforation tool 48 may be designed as described above and, hence may be a hollow needle or a solid needle and may be configured to fixate an anchor 50 and/or a chord 52 with the tissue 6 of the valve 4. FIG. 4c shows the flexible perforation tool 48 with anchor 50 and chord 52 attached to its tip while perforating tissue 6 to thereby fixate anchor 50 in the tissue 6 of the valve 4. The end of the chord 52 opposite to the anchor 50 can e.g. be attached to surrounding tissue, for example in the papillary muscle or the ventricular apex, at the discretion of the operator.

In other embodiments, the perforation tool 48 can be configured to deliver drugs or other substances to the tissue of the valve 4.

In other embodiments, the perforation tool or a needle 48 may not be provided in an inner lumen 60 of a wire 38 forming the cage body 36, but may be separate from the cage 36 and be independently forwarded through the inner lumen of the catheter member 8 and operable independently.

FIG. 4d shows the treatment catheter system 2 after the anchor 50 has been fixated to the tissue of the valve 4. A radial distance D1 between the elongate flexible outer member 28 and the catheter member 8 has been increased by releasing the previously radially contracted elongate flexible outer member 28, and the catching component 20 (comprising the wire cage body 36) is partially retracted into the distal end portion 16 of the catheter member 8 and has been removed from the heart valve 4 and the elongate flexible outer member 28. The tissue of the heart valve 4 that is immobilized between the lateral groove 22 and the elongate flexible the elongate flexible outer member 28 may be released by increasing the distance between catheter member 8 and the elongate flexible outer member 28 by operating the catching mechanism 32 (i.e. the length of the elongate flexible outer member 28 is increased resulting in larger circumferential length of the elongate flexible outer member 28). In other embodiments, the tissue 6 of valve 4 may be released by retracting catching component 20 including wire cage 36 back into the distal end portion 16 of catheter member 8 (i.e. reducing the circumferential diameter of lateral groove 22). In some embodiments, the catching mechanism 32 is operated to increase the circumferential length of the elongate flexible outer member 28 and the catching component 20 is retracted at the same time in order to release the tissue 6 caught between lateral groove 22 and the elongate flexible outer member 28.

Figure 5:
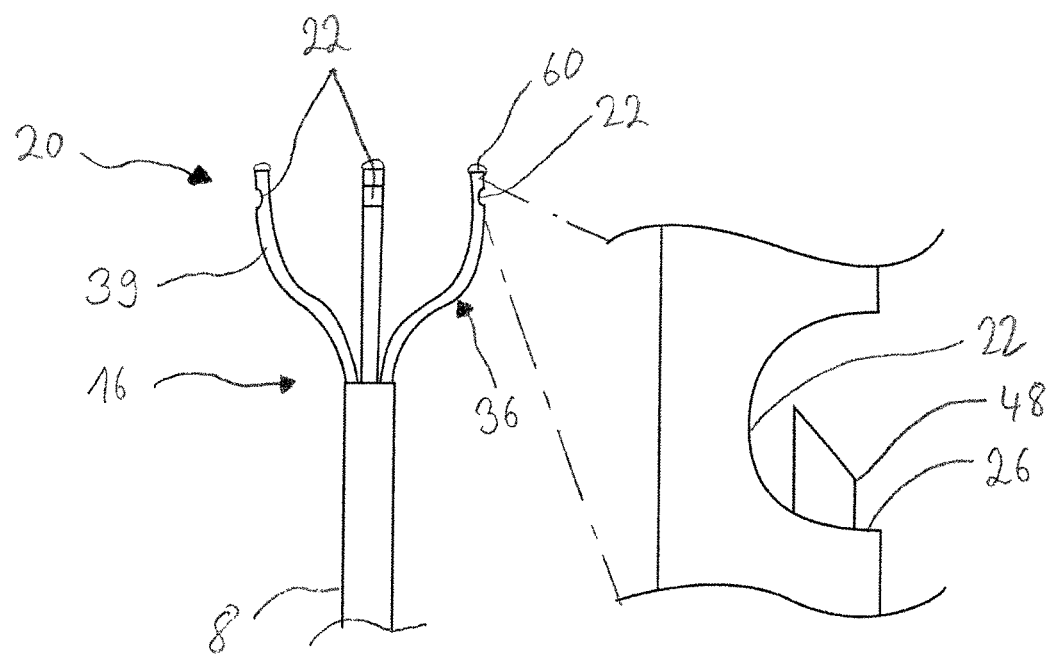
FIG. 5 schematically shows a catheter member of a treatment catheter system according to an embodiment.

FIG. 5 shows an embodiment of a catheter member 8 of a treatment catheter system 2 according to an embodiment. The embodiment is similar to the embodiments described with reference to FIGS. 4a to 4c. In this embodiment, however, the lateral groove 22 is formed by the sheaths 39 forming the cage body 36 of catching component 20, the sheaths 39 having a respective lateral recess therein at the level of the lateral groove 22 thereby circumferentially forming the lateral groove 22 in an interrupted manner. The wire cage body 36 is retractable into the distal end portion 16 of catheter member 8 and can be expanded from a retracted position. The tips of the sheaths 39 forming the cage 36 are shown in FIG. 5 as being straight/blunt, whereas they may also be conical. The interaction of the catheter member 8 and the elongate flexible outer member 28 (not shown in FIG. 5) to catch and immobilize tissue 6 of a heart valve 4 (not shown in FIG. 5) in the lateral groove 22 via the lateral catching opening 26 is similar to the embodiments described previously. The sheaths 39 forming the cage 36 have an inner lumen 60 allowing forwarding and retracting a flexible perforation component 48, e.g. a needle 48, through the lumen 60 into the lateral groove 22 and back into the lumen 60 of the sheaths 39 forming the cage body 36. One or more of the sheaths 39 may also be substituted by a solid body, for example a wire having no inner lumen.

While FIG. 5 shows an embodiment where the lateral groove 22 is formed or defined by a recess on each sheath 39 forming the cage body 36, there may be other embodiments where only one or only some of the sheaths 39 forming the cage body 36 comprise a recess forming/defining the lateral groove 22. In this respect, when a radial distance D1 between the elongate flexible outer member 28 and the catheter member 8 is reduced, tissue is only firmly caught and immobilized on those sheaths 39 forming the cage body 36 that comprise a recess defining the lateral groove 22.

The elongate, flexible perforation tool 48, e.g. a needle or hollow needle 48, is configured to perforate or puncture the caught valve tissue 6 or adjacent valve tissue in order to attach an anchor with or without a chord, e.g. as previously described (not shown in FIG. 5), to the valve tissue 6 or tissue adjacent to the valve 4. For this, an anchor with or without an attached chord may be seated on the tip of the hollow needle 48 and the chord may be led through the lumen of the hollow needle 48 (only if the embodiment comprises a chord).

The hollow needle 48 loaded with anchor and chord is contained in the inner lumen 14 of the catheter member 8 and can be controlled by an interventional cardiologist or a surgeon to move forward towards the distal end 16 and en route perforate valve tissue caught in the lateral groove 22. Afterwards, the needle 48 can similarly be controlled to be fully retracted backwards towards the proximal end portion 18 (cf. FIG. 1) so that it is fully sheathed in the lumen 60 of the sheaths 39 forming the cage body 36. The anchor remains seated in the valve tissue 6 with the chord extending from the anchor. In some embodiments, the other end of the chord on the side opposite to the anchor is fixated e.g. to tissue surrounding the valve 4.

In FIG. 5, the hollow needle 48 without an anchor or chord is shown in an intermediate position with its tip extending into the lateral groove 22.

With reference to FIG. 6, another embodiment of a catheter member 8 of a treatment catheter system 2 is shown. The catheter member 8 shown in FIG. 6 is and operates similar to the one shown in FIGS. 4a to 4d and comprises a catheter member 8 having a distal end portion 16 with a catching component 20, a wire cage 36, a temporary artificial heart valve 42, a substantially non-compressible front body 44 and a leading wire or string 58. The temporary artificial heart valve 42 is arranged within the cage 36 and is fixedly attached to the inner side of the cage 36. In the expanded condition of the cage 36, the temporary artificial heart valve 42 is deployed from a compressed condition and can temporally take over the function of the native valve 4 as long as the catching component 20 is positioned within the interior of the circumferential valve tissue structure 6. A lateral sealing function is achieved by the engagement of the valve tissue structure 6 within the circumferential lateral groove 22. The embodiment shown in FIG. 6 further comprises an additional reinforcing mesh 62. The mesh 62 may be made from flexible wire, thread, polymer or any other material and is connected to the sheaths 39 of the wires 38, the sheaths 39 also contribute to forming the cage 36 at a distal end portion of the cage 36 in a way that it forms a tubular mesh-liner 62 inside the cage body 36 when the catching component 20 is extended from the catheter member 8. The mesh 62 may improve the mechanical stability of the cage body 36 and/or the mechanical stability of the temporary artificial valve 42. Embodiments that do not feature a temporary artificial heart valve 42 (e.g. the embodiment shown in FIG. 5) also can comprise a mesh 62 as described above in order to improve mechanical properties.

In other embodiments, instead of an anchor, drugs or other substances (e.g. to improve medical imaging) and/or devices for treatment or interaction can be applied to the caught valve tissue 6 by one or more needle(s) 48 in the catching component 20. In some embodiments, the needle(s) 48 can be exchangeable so that an optimal needle can be chosen to e.g. attach an anchor 50 to the valve tissue 6 or deliver drugs or so that the needle 48 can be replaced once the tip of the needle 48 is worn after use. In all embodiments, the elongate perforation component(s) 48 (e.g. the needle(s) 48) may be flexible.

In any or all embodiments, the perforation component 48 may comprise a lumen 60 through which a medical drug supplying component 64, e.g. a hollow needle 64, can be forwarded and retracted to deliver drugs or substances. This enables the treatment catheter system 2 according to some embodiments to use the perforation component 48 to attach an anchor 50 to and/or interact with tissue of the valve 4 and then forward a hollow needle 64 via the perforation component 48, i.e. the perforation component 48 serves two functions: to interact with tissue of the valve 4 and to serve as a sheath for a hollow needle 64 to deliver drugs or substances. The medical drug may also be forwarded directly through the inner lumen 60 of the hollow perforation component 48.

Some of the sheaths 39 containing wires 38 for forming the cage 36 may be configured to allow forwarding of an anchor 50 with or without a chord 52 therethrough, while at the same time other sheaths 39 may be configured to deliver drugs and/or other substances.

While the cage 36 is shown in FIGS. 4a to 4c and FIGS. 5 to 6 to comprise four wires 38, in other embodiments it can comprise one wire, two wires, three wires, five wires or a plurality of wires 38, depending on the operational needs.

Similarly, the wires 38 forming cage 36 can be arranged on a (same) circle, each having the same or a different angular distance from each other. If the cage 36 comprises four wires 38, these can be arranged on a circle having an angular distance of 90 degrees each from each other. In other embodiments, they can be arranged on a circle having arbitrary angular distances between each other, e.g. 170 degrees between a first and a second wire, 30 degrees between the second and a third wire, 69 degrees between the third and a fourth wire (which results in an angle of 360 degrees–170 degrees–30 degrees–69 degrees=91 degrees between the fourth wire and the first wire). Therefore, two or more sheaths 39 may be arranged to have a small angular distance, e.g. smaller or equal 1 degree, 5 degrees, 10 degrees or 15 degrees. Therefore, it is possible to deliver a drug or substance through a first sheath 39 so that the area in which the anchor 50 is fixated (through a second sheath 39) can be treated with a drug or substance before the anchor 50 is fixated, while the anchor 50 is fixated or after the anchor 50 is fixated.

In other embodiments, the wires 38 are not forming a substantially round cage 36 as shown in FIG. 4a to FIG. 4c and FIGS. 5 to 6, but e.g. a triangular-shaped cage 36, a rectangular-shaped cage 36 or a polygonal-shaped cage 36.

In yet other embodiments, the cage 36 may comprise a plurality of sheaths 39, but not all sheaths 39 may be configured to guide forwarding and/or retracting of a perforation component 48 through their inner the lumen 60. If e.g. the cage 36 comprises four sheaths 39, only one or two or three sheaths 39 may be configured to guide forwarding and/or retracting of a perforation component 48, while the remaining sheath(s) 39 may not comprise an inner lumen 60 (i.e. may be solid bodies).

One or more additional perforation components 48 may be provided that can be extended separately and independently from the wires 38 of the wire cage 36 out of the distal end portion 16 of the catheter member 8.

None of the sheaths 39 may comprise a perforation component 48 and there may only be one or more perforation component(s) 48 that can be extended from the distal end portion 16 of the catheter member that are separate and independent from the sheaths 39.

Some embodiments of the treatment catheter system 2 may comprise an inflatable balloon coated with drugs or substances in the distal end portion 16 of the catheter member 8. The balloon can be forwarded through the inner lumen 14 of the catheter member 8 and can be inflated by the operator to come in contact with heart tissue, thereby delivering the drugs on its surface to the tissue it is in contact with. The balloon may also be deflatable by the operator in order to facilitate retraction of the catheter member 8 from the heart.

All embodiments of the catheter member 8 may be configured to deliver drugs or other substances to heart tissue and/or other tissue. Such substances can for example comprise a plasmid coding for a certain protein. The protein can e.g. be expressed by the native leaflet cells and can serve as a treatment of the leaflet 4 or surrounding tissue. For that purpose, an adequate electrical field or other energy source may be applied between the elongate flexible outer member 28 and the catching component 20 in order to achieve the opening of holes in the cell membrane (e.g. electro-poration) to promote plasmid entry inside the cells. The elongate flexible outer member 28 and the catching component 20 may comprise electrodes (or, as an alternative, if they are made from electrically conducting materials like metals, may act as electrodes themselves without comprising additional electrodes) that are connected to an electric energy source via electrically conducting means, e.g. via electric wires that are sheathed in an inner lumen 14 of catheter member 8 and/or are sheathed in an inner lumen of outer member catheter 29, respectively. The catheter member 8 and/or the outer catheter member 29 may serve as electrically conducting means without additional means like wires if they are made from an electrically conducting material. The energy source may be placed outside the human body and may comprise a control means to selectively control voltage, current and/or direction of the current of the electric energy source. The energy source may be a battery (e.g. producing a direct current (DC)) or may be an alternator (e.g. producing alternating current (AC)) or may be any other source of AC and/or DC electric current. The electric charge of catching component 20 may have an electric polarity opposite to a polarity of the elongate flexible outer member 28 (and/or their respective electrodes). The control means may e.g. produce a square-wave voltage or a sawtooth voltage or a sine-shaped voltage or any other periodic or non-periodic voltage that may be conducted to the electrodes of the elongate flexible outer member 28 and/or the catching component 20 (or to the elongate flexible outer member 28 and/or the catching component 20 themselves, if they do not comprise additional electrodes but act as electrodes themselves) via the electrically conducting means or via the catheter member 8 and/or the outer catheter member 29 themselves, if they are made from electrically conducting material. The electric field that thereby may be established between the elongate flexible outer member 28 and the catching component 20 (e.g. between their respective electrodes) may interact with tissue and open holes in the cell membranes of cells, e.g. of cells that form the heart valve 4 and/or a papillary muscle of a heart and/or any other heart cell so that substances may diffuse or be moved by the electric field through the open holes into the inside of cells. The holes may close again, when voltage and/or current of the electric energy source are interrupted by the control means on the discretion of an interventional cardiologist or a surgeon, resulting in the substance being "caught" in the cells. Substances can include substances that improve medical imaging, e.g. substances containing radioactive isotopes or substances changing electromagnetic properties of the tissue in order to improve visibility and/or contrast using electro-magnetic imaging techniques such as X-ray imaging (e.g. angiography or echocardiography), magnetic resonance imaging or other medical visualization techniques.

In embodiments of the catheter member 8, the catching component 20 which is or can be positioned at the distal end portion 16 of the catheter member 8 is designed to be non-separable from the catheter member 8, at least when positioned at the distal end portion 16 of the catheter member 8.

Figure 14:
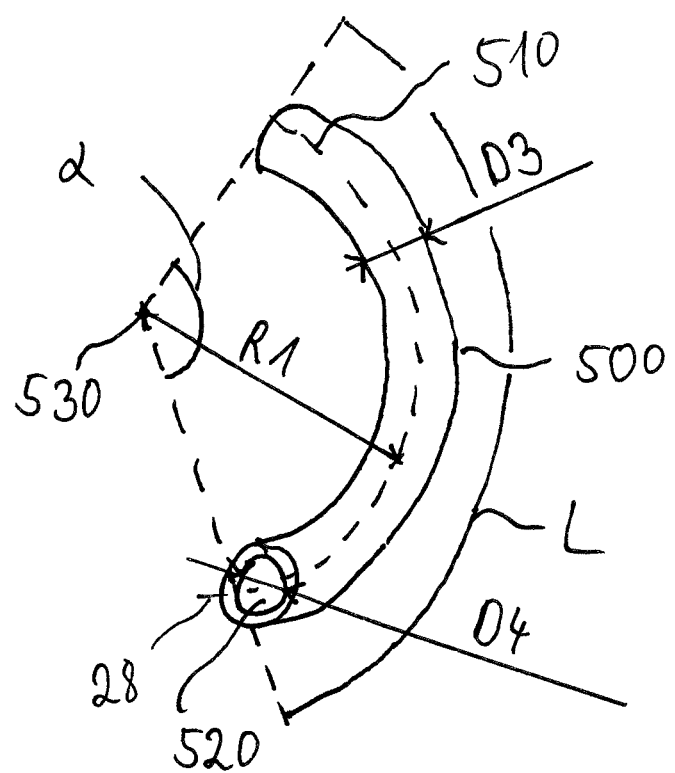
FIG. 14 shows an exemplary embodiment of a prosthesis that is implantable using the treatment catheter system.

With further reference to FIGS. 13a, 13b and 14, the treatment catheter system 2 according to the present invention may be used to interact with one or several prosthesis 500, e.g. to implant the prosthesis 500. Accordingly, the prosthesis 500 may optionally be a part of the treatment catheter system 2. The prosthesis 500 may generally be flexible. The prosthesis 500 may generally have a toroidal shape (e.g. when no substantial external forces act on it) having a longitudinal axis 510 and an outer diameter D3 that is defined substantially perpendicular to longitudinal axis 510. The prosthesis 500 may have a curvature and an outer diameter D3 that is corresponding to the catching opening 26 and/or the lateral groove 22 so that the prosthesis 500 may be configured to be located in the lateral groove 22, for example in addition to tissue (e.g. of circumferential tissue structure 6) and/or the elongate outer member 29. That is, diameter D3 of prosthesis 500 may be equal to a width of lateral groove 22 in a direction of longitudinal axis 12 or may be smaller (for example, D3 plus a thickness of the tissue of the circumferential tissue structure 6 of a human heart multiplied by two may be equal to the width of the lateral groove 22 along longitudinal axis 12). The dimensions of the prosthesis 500 may further be defined by a radius R1 that is defined between a central point 530 (which may be a point on the longitudinal axis 12 of the catheter member 8 for example when the prosthesis 500 is at least partially forced into the lateral groove 22 as it is described below) and the longitudinal axis 510 and an extension angle α that is defined between two end portions (in a direction along longitudinal axis 510) of the prosthesis 500. The extension angle may define a full circle (i.e. 360°) or less than a full circle, e.g. approximately 5 to 15°, 15° to 30°, 30 to 45°, 45° to 60°, 60° to 80°, 80° to 110°, 110° to 150° or 150° to 180° or any combination or subset of the mentioned intervals or any other angle. The prosthesis 500 may also have a length L along longitudinal axis 510 that is defined between the two end portions (L, α, D3 and D4 may geometrically be related to each other, c.f. FIG. 14). With respect to length L that is depicted in FIG. 14, it must be noted that L describes the length of prosthesis 500 along its longitudinal axis 510 when it is straight and not bent and not a length of an arc. In this respect, the prosthesis 500 may generally describe a "C-shape". Further, the geometric dimensions of the prosthesis 500 may be selectively changeable, i.e. D3, R1 and/or α may be selectively changeable, e.g. on the discretion of a surgeon. The prosthesis 500 may comprise and inner lumen 520 that may be extending from one end portion to the other end portion of prosthesis 500 along longitudinal axis 510. In this respect, D3 may define the outer diameter of the prosthesis 500 and a diameter D4 may define the inner diameter (i.e. the 'outer' diameter of inner lumen 520). The inner lumen 520 and its diameter D4 may be configured so that the prosthesis 500 may be surrounding, e.g. at least partially or fully surrounding, the outer member 29. For example, the prosthesis 500 may be adapted so that it can slide along the elongate flexible outer member 28 while being beaded on the elongate flexible outer member 28 with inner lumen 510 surrounding the elongate flexible outer member 28. Accordingly, the prosthesis 500 may be flexible so that it may follow a curvature of the elongate flexible outer member 28 when sliding over the elongate flexible outer member 28. The prosthesis 500 may be adapted to be fixed to tissue of the circumferential valve tissue structure 6 and/or to the annulus 4c of a heart valve 4, for example using hooks, clips or screws 530 as shown in FIGS. 13a and b or by other means. In this respect, the prosthesis 500 and the inner lumen 520 thereof may be adapted so that clips or screws 530 or other means of fixation may be forwarded from a position outside the heart to the prosthesis 500 via the elongate flexible outer member 28. The prosthesis 500 may also be provided with means to fix clips or screws 530 to tissue of a valve 4 in order to fixate prosthesis 500 to that tissue.

The prosthesis 500 may be adapted to be a sub-annular prosthesis (i.e. a prosthesis, that is adapted to be placed and/or fixated close to heart valve 4 (e.g. the annulus 4c thereof) on a side of the ventricular chamber 4b of heart valve 4) and may serve to change a perimeter of the natural annulus 4c, e.g. to reduce the perimeter or modify the shape of the annulus 4c in order to treat valve insufficiency. In this respect, the prosthesis 500 may be adapted to carry out annuloplasty (i.e. annuloplastic surgery). Further below an exemplary method of using a treatment catheter system 2 including a prosthesis 500 to carry out annuloplasty will be described.

All embodiments of the treatment catheter system 2 may comprise positioning and/or orientation devices to facilitate relative and/or absolute positioning of the catheter member 8 and the elongate flexible outer member 28. These devices may include passive markers (e.g. marker members) that are fixedly attached to catheter member 8 and/or the elongate flexible outer member 28. The passive markers may be made from materials different from the materials of the catheter member 8 and/or the elongate flexible outer member 28 in order to improve contrast during medical imaging, e.g. using magnetic resonance or X-ray based imaging techniques. The passive markers may e.g. be made of highly radio-opaque materials thereby allowing to precisely acquire the relative and/or absolute position of the components of the treatment catheter system 2 with respect to the body. The passive markers may have an asymmetrical shape to allow identifying the absolute and/or relative position and orientation and thereby the position and orientation of the catheter member 8 and/or the elongate flexible outer member 28. The lateral groove 22 of the catheter member 8 and/or the elongate flexible outer member 28 may have passive markers fixedly attached to facilitate positioning them relative to each other using imaging techniques, e.g. passive markers made of highly radio-opaque materials when imaging techniques based on electro-magnetic radiation (e.g. X-ray imaging) are used. In addition and/or as an alternative, the lateral groove 22 and/or other parts/components of the catheter member 8 and/or the elongate flexible outer member 28 may be made from radio-opaque materials. Other positioning and/or orientation devices can include "active devices", i.e. devices that emit and receive a signal, e.g. an ultra-sonic signal or a X-ray signal or generally an electro-magnetic signal and are configured to determine relative and/or absolute positions of the components (e.g. the catheter member 8 and the elongate flexible outer member 28) of the surgical tools system 2 and/or organs of the human/animal body (e.g. the heart) and/or parts of organs of the living body (e.g. a mitral valve 4). These active devices may be a part of the catheter member 8 and/or the outer member catheter 29 or the elongate flexible outer member 28 or some components (e.g. signal generator, transmitter and/or receiver) of the active devices may be a part of the catheter member 8 and/or the outer member catheter 29, while other components (e.g. a signal processing device and/or a display device) of the active devices may be placed outside the human body. The catheter member 8 may also comprise a metal detector capable of detecting metals (e.g. by using an alternating electric current passing through a wire coil and measuring the resulting magnetic field, which is a function of size, distance and/or material of surrounding matter). The elongate flexible outer member 28 may comprise passive markers or consist of a material with a high magnetic permeability (e.g. iron, nickel, cobalt) to facilitate detection by a metal detector, that is e.g. positioned in the catheter member 8, and to thereby allow measuring a distance and/or relative position between elongate flexible outer member 28 and catheter member 8. The catheter member 8 an/or the outer member catheter 29 may also comprise a glass fiber attached to a lens system provided on the distal end portions thereof to allow optical detection of an absolute or relative position of catheter member 8 and the elongate flexible outer member 28. The glass fiber and lens system may also be configured to transmit light from an external light source into the heart. The distal end portions of catheter member 8 and/or outer member catheter 29 may also comprise active light sources, e.g. light emitting diodes. In all embodiments, the outer member catheter 29 and/or the catheter member 8 may comprise an ultra-sound generator, transmitter and receiver to send and receive ultra-sonic audio signals in order to obtain sonograms of the valve 4, catheter member 8 and/or elongate flexible outer member 28. In some embodiments, "active" and "passive" means are used operating together, i.e. the imaging capability of an active means device is improved by using adequate "passive" markers. In some embodiments, only passive "markers" together with external imaging (e.g. a signal generator, signal transmitter and signal receiver positioned outside the living body) are used.

A method of immobilizing a circumferential heart valve tissue structure for example using the treatment catheter system as described above may comprise:

arranging an elongate, for example flexible, outer member 28 to fully or only partially extend around a perimeter of a circumferential heart valve tissue structure, arranging a catheter member 8, on which a lateral groove 22 opens towards the lateral outside of the catheter member, at the interior of the circumferential heart valve tissue structure, in a manner so that the outer member 28 and the lateral groove 22 are aligned with each other, reducing a radial distance D1 between the outer member 28 and the catheter member 8 to force valve tissue of heart valve tissue structure 6 into the lateral groove 22 to catch and to thereby immobilize valve tissue 6 in the lateral groove 22 of the catheter member 8.

The method may further comprise one or more of:
removing the catheter member 8 and/or the outer member 28 form the heart valve 4, arranging the outer member 28 to fully extend or only partially extend around, e.g. only around one quarter or one third or one half or three quarters around an outer perimeter of circumferential heart valve tissue structure 6.

To place catheter member 8 and/or the outer member 28 at the heart valve, the following approaches may be applied: 1) an arterial retrograde approach (e.g. the femoral artery through a puncture in the groin) entering the heart cavity over the aorta, 2) through a venous access possibly associated with a puncture through the inter atrial septum (trans-septal approach), 3) over a puncture through the apex of the heart (trans-apical approach), 4) over a puncture through the atrial wall from outside the heart, or 5) any other approach known to a skilled person.

Further, the method may comprise forwarding a catching component including the lateral groove 22, the catching component 20 may be formed by a grid-type or mesh-type cage 36, through an inner lumen 14 of the catheter member 8 to be exposed to the outside at the distal end portion 16 of the catheter member 8.

In one embodiment, the method may comprise a method for surgical treatment of a bloodstream valve 4 having a circumferential valve tissue structure 6. The method may comprise advancing a treatment catheter system 2 as described above into a vicinity of the bloodstream valve 4 placing the lateral groove 22 of the catheter member 8 in an interior 10 of the circumferential valve tissue structure 6; placing the elongate outer member 28 at least partially around an outside of the circumferential tissue structure 6 at an axial level, with respect to the longitudinal axis 12, of the lateral groove 22; reducing a distance D1 between the elongate outer member 28 and the lateral groove 22 so as to at least partially force tissue of the circumferential valve tissue structure 6 into the lateral groove 22; and removing the catheter member 8 and the elongate outer member 28 from the patient.

The outer member 28 (which may be sheathed in an outer member catheter 29) and the catheter member 8 may be inserted via the same insertion approach or inserted using a different approach for outer member 28 and catheter member 8 respectively.

Reducing the radial distance D1 between outer member 28 and catheter member 8 may comprise reducing a distance D1 by reducing a length of the outer member 28 and/or by increasing a diameter of the cage 36, e.g. by using a catching mechanism 32.

Further interaction and/or treatment may comprise fixating one or more anchors 50 or anchors 50 with chords 52 to tissue, delivering substances or drugs and/or medical imaging. Further, a temporary artificial heart valve 42 may be forwarded to the heart valve 4 during interaction and/or treatment as described above in order to prevent valve insufficiency, the temporary artificial heart valve 42 may be fixedly attached to the catching component 20. Fixating anchors 50 and delivery of substances or drugs may comprise using a perforation tool 48 as described above. Medical imaging may comprise using active and/or passive means as described above. Fixating one or more anchors 50 may include to join two, three, four, five or a plurality of tissue layer together.

Removal of the catheter member 8 and/or the outer component 28 may comprise retracting the cage 36 and/or the temporary artificial heart valve 42 into the distal end portion 16 of the catheter member 8, thereby increasing a radial distance D1 between outer member 28 and catheter member 8. Removal may also comprise increasing a radial distance D1 between outer member 28 and catheter member 8 by increasing the length of the outer member 28, e.g. by using the catching mechanism 32 or by straining the outer member 28 (i.e. using elastic properties of the outer member).

The catheter member 8 and/or the outer member 28 may be retracted from the heart using the same approaches through which they were inserted.

Figure 7:
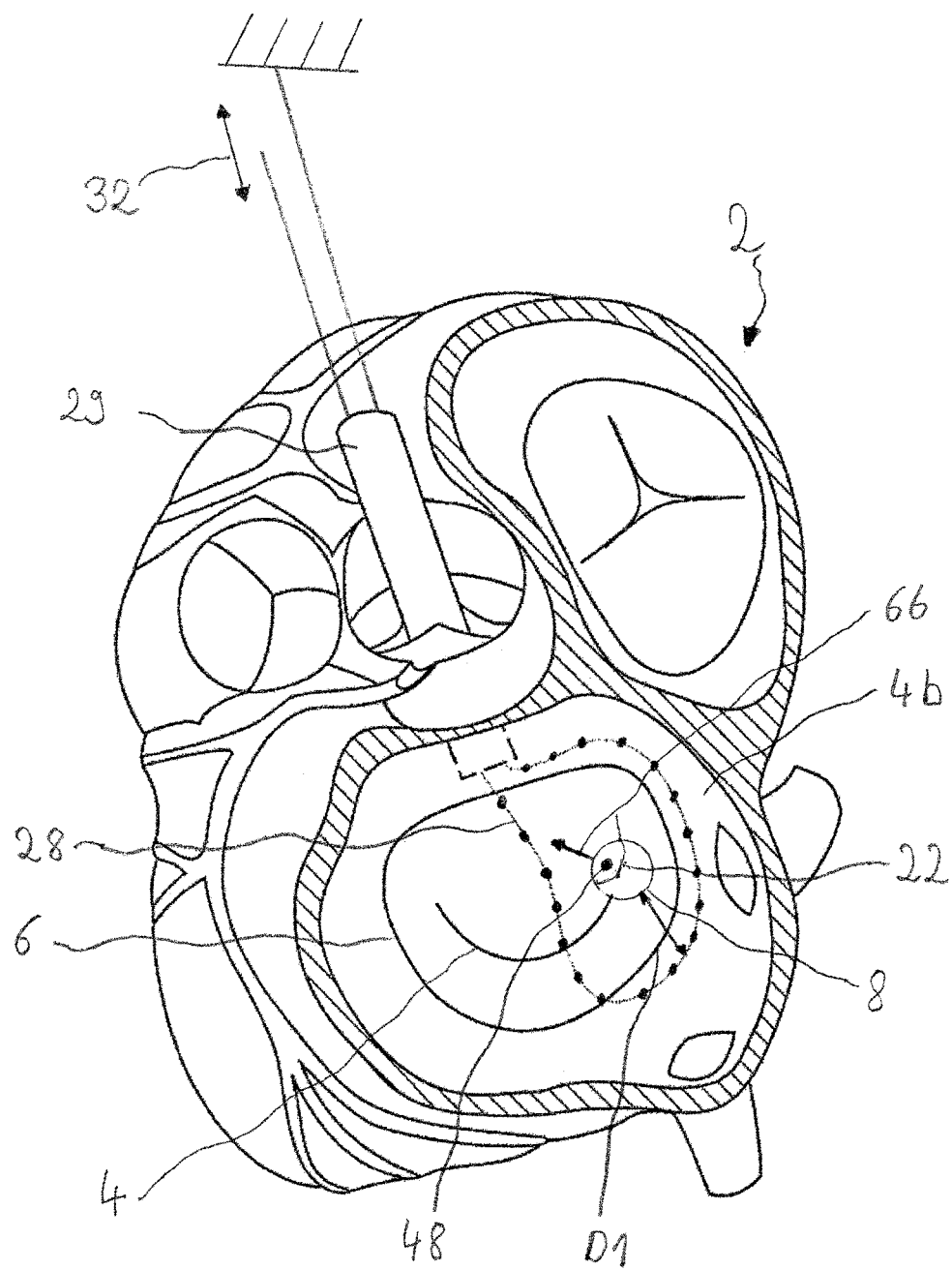
FIGS. 7-9 illustrate a method for using a treatment catheter system according to an embodiment.
Figure 8:
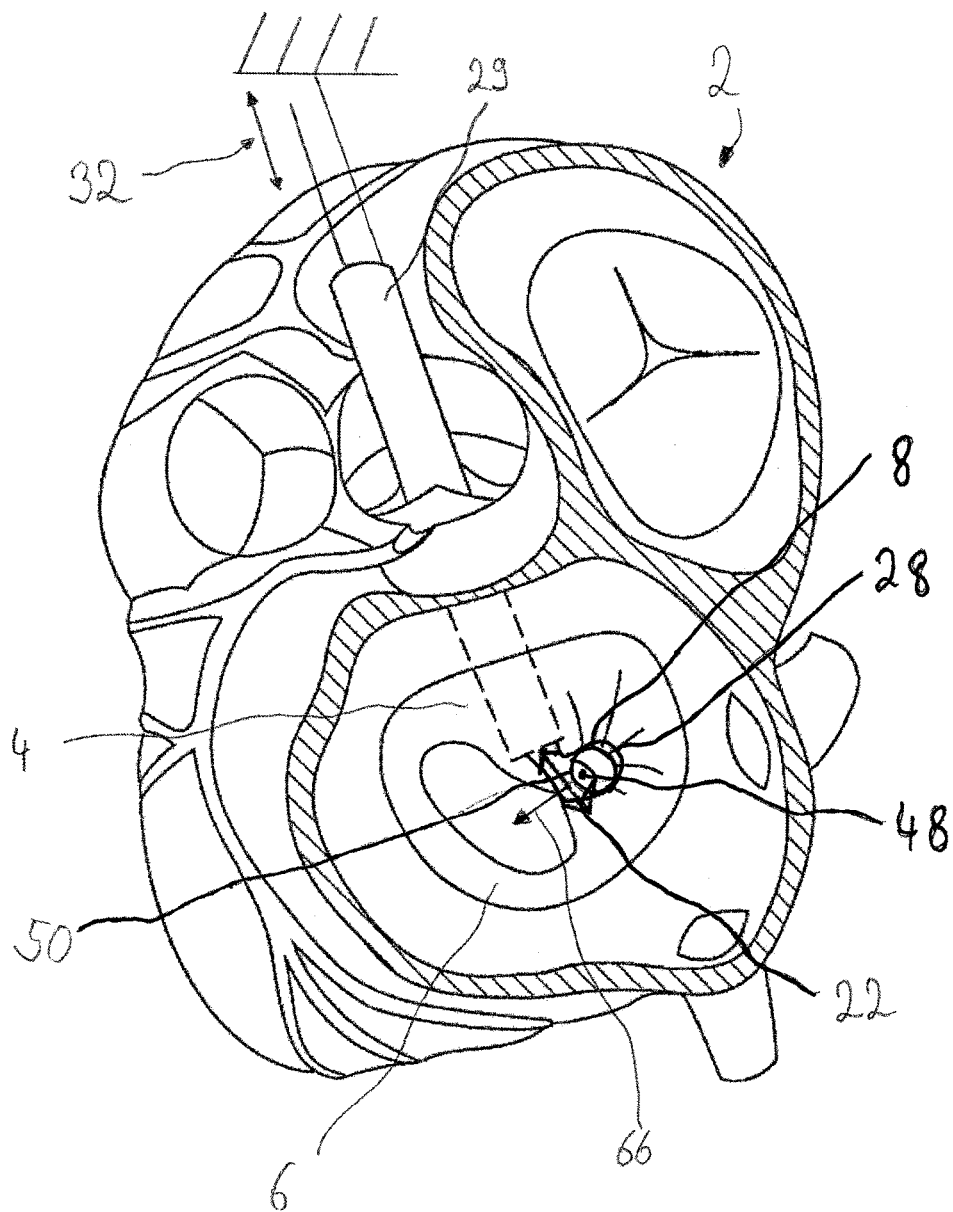
Figure 9:
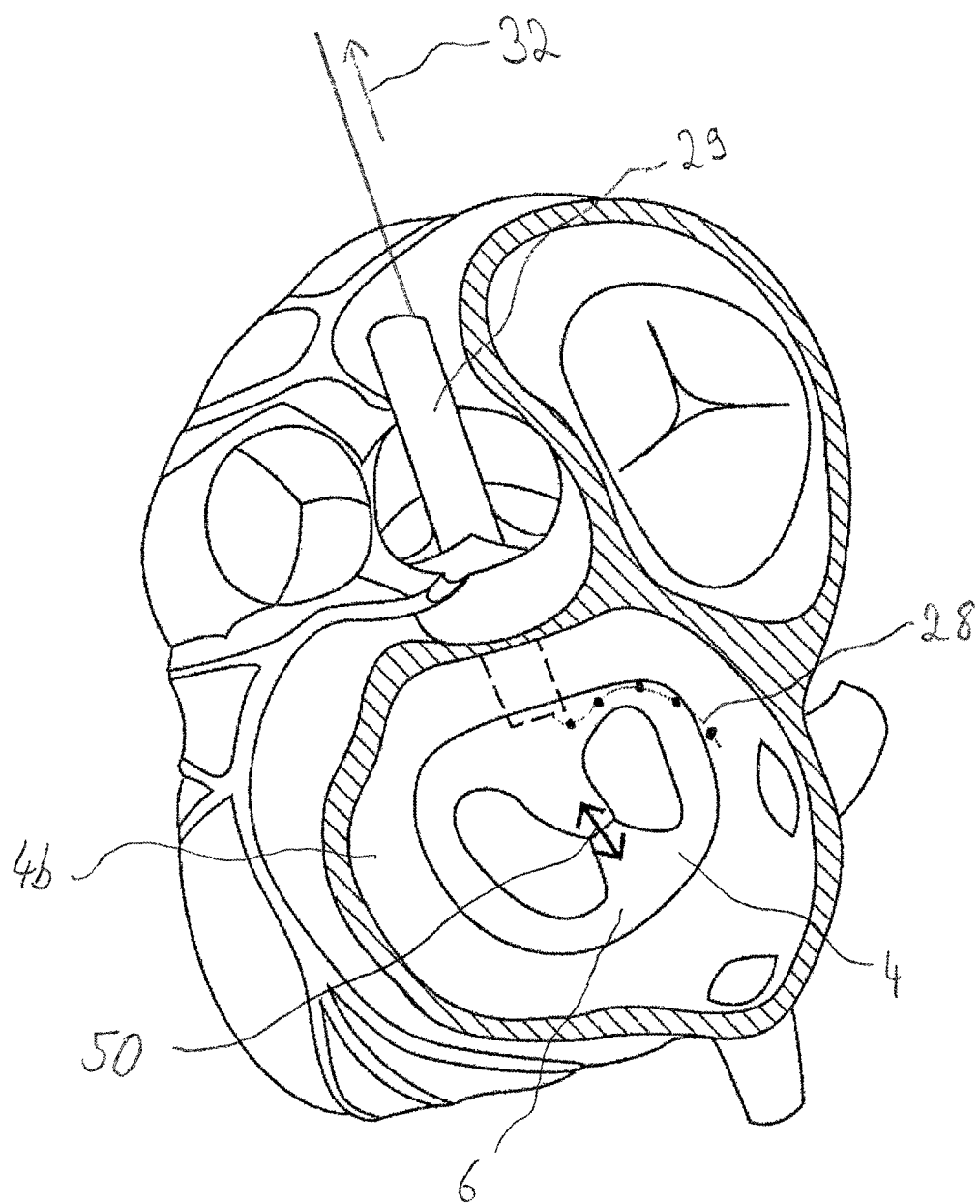

With reference to FIG. 7 to FIG. 9, exemplary methods for using the treatment catheter system 2 are described. One exemplary method described is called the "Alfieri technique" and is used to create two separate openings for the blood to flow through the native leaflets 4 of the mitral valve.

FIG. 7 shows a view of a human heart with a view from the left atrial chamber 4b onto the mitral valve 4. The elongate flexible outer member 28 located on the ventricular side of the mitral valve 4 (i.e. in FIG. 6 below the mitral valve 4) is indicated by a dotted line. The elongate flexible outer member 28 is arranged to only partially surround the circumferential mitral valve tissue structure 6 in the ventricular chamber 4a (see FIG. 1) and to extend diametrically transverse to the longitudinal direction of the circumferential heart valve tissue structure 6. However, in other embodiments, the elongate flexible outer member 28 may be arranged to fully extend around a perimeter of a heart valve 4. In FIG. 7, the catheter member 8 can be seen extending from the ventricular chamber 4a via the mitral valve 4 to the atrial chamber 4b. Arrow 66 indicates the position and orientation of the catching opening 26 of the lateral groove 22 of the catheter member 8. The elongate flexible outer member 28 is inserted via percutaneous approach and the catching mechanism 32 that is configured to decrease or increase a radial distance D1 between the elongate flexible outer member 28 can be schematically seen outside the heart.

FIG. 8 shows a further stage of the method for using the treatment catheter system 2. FIG. 8 shows a view of the human heart with a view from the left atrial chamber 4b onto the mitral valve 4. The elongate flexible outer member 28 located on the ventricular side of the mitral valve 4 (i.e. in FIG. 6 below mitral valve 4) is indicated by a dotted line. The catheter member 8 can be seen extending from the ventricular chamber 4a via the mitral valve 4 to the atrial chamber 4b Arrow 66 indicates the position and orientation of the catching opening 26 of the lateral groove 22 of the catheter member 8. A radial distance D1 between the elongate flexible outer member 28 and the catheter member 8 has been reduced by the catching mechanism 32, resulting in that heart valve circumferential tissue from two diametrically opposite sides of the circumferential heart valve tissue structure 6 of the mitral valve 4 is caught and immobilized in the lateral groove 22 via the catching opening 26. The perforation component 48 is equipped with an anchor 50 (schematically shown) in order to fix tissue of two diametral sides of the valve 4 together. The perforation component 48 equipped with the anchor 50 as described above is extended to perforate the tissue caught and immobilized in the lateral catching groove 22. When the perforation component 48 is retracted afterwards, the anchor 50 stays in place and fixes the tissue 6 of two diametral sides of valve 4 together.

FIG. 9 shows a further stage of the method for using the treatment catheter system 2. FIG. 9 shows a view of the human heart with a view from the left atrial chamber 4b onto the mitral valve 4. The elongate flexible outer member 28 located on the ventricular side of the mitral valve 4 (e.g. in FIG. 6 below mitral valve 4) is indicated by a dotted line. In FIG. 9, a radial distance D1 between the elongated flexible outer member 28 and the catheter member 8 has been increased, releasing the valve tissue 6 caught and immobilized in the lateral groove 22. Then, the catheter member 8 is moved away from the vicinity of the valve 4 and is no longer visible in FIG. 9. Eventually, the catheter member 8 is removed completely from the body. However, anchor 50 remains fixated to the valve tissue 6 joining together tissue from two diametral sides of the valve 4. The elongate flexible outer member 28 is shown in the process of being retracted from the heart. Once the elongate flexible outer member 28 is fully retracted from the heart, a method for using a treatment catheter system 2 according to one embodiment is completed, leaving only an anchor 50 that is joining together tissue 6 of to diametral sides of the mitral valve 4 behind in the heart.

Using the treatment catheter system 2 as described above to immobilize tissue may enable attachment of a prosthesis to the immobilized tissue. Such a prosthesis may not be part of the treatment catheter system 2 or it may be a part of the treatment catheter system 2. According to an aspect of the invention as described below, the elongate flexible outer member 28 may not only serve to force tissue into the lateral groove 22, but may also serve to guide a prosthesis to an intended location close to a bloodstream valve 4. According to aspects of the invention the catheter member 8 (e.g. the catching component 20, e.g. the catching component 20 when formed as a wire cage 36) may be provided with a temporary artificial heart valve 42 so that a valve function of the valve 4 that is to be treated (and is e.g. immobilized) is provided while the treatment catheter system 2 is used. This may enable prolonged operation times without damage to a patient due to interrupted blood circulation, which in turn allows a surgeon to more efficiently carry out treatment due to reduced time constraints.

With further reference to FIGS. 13a, 13b and 14, a method to carry out surgical treatment of tissue of a heart valve 4 is described. The method may comprise catching and immobilizing tissue of the heart valve 4 (e.g. the circumferential valve tissue structure 6) via the catching opening 26 in the lateral groove 22 substantially as described above. More specifically, the method may comprise placing catheter member 8 having a catching component 20 (e.g. formed as a cage body 36) with a lateral groove 22 as described above close to the heart valve 4, e.g. close to mitral valve 4 on the side of the ventricular chamber 4a, on the interior 10 of circumferential valve tissue structure 6 using an approach as described above, e.g. an approach via the apex of the heart. During the approach to the position close to the heart valve 4, the catching component 20 (including lateral groove 22) may be retracted into the inner lumen 14 of catheter member 8. If this is the case and when the position close to the heart valve 4 is reached, the method may optionally (e.g. when the catching component 20 is moveable relative to the catheter member 8) comprise forwarding the catching component 20 from the inner lumen 14 of catheter member 8 in a distal direction of longitudinal axis 12 in order to expose the catching component 20 (e.g. formed as a cage body 36) having the groove 22.

The method may further comprise placing the lateral groove 22 close to the annulus 4c of the heart valve 4. According to aspects of the invention, the groove 22 may be placed on the ventricular side 4a of the annulus 4c (sub-annular placement). In this respect, the groove 22 may be placed by moving the catheter member 8 relative to the annulus 4c and/or by moving the catching component 20 (that may e.g. be formed as a wire cage 36) relative to the catheter member 8.

Before, while or after the lateral groove 22 is placed as described above, the method may also comprise using the outer member catheter 28 (and/or other means) to place the elongate flexible outer member 28 at least partially or fully around tissue of the circumferential valve tissue structure 6 (that is on the outside of circumferential tissue structure 6, i.e. e.g. between circumferential tissue structure 6 and a wall of the ventricular chamber 4a). The method may comprise placing the elongate flexible outer member 28 on the outside of the circumferential tissue structure at an axial level (axial e.g. with respect to the longitudinal axis 12 of the catheter member 8) of the lateral groove 22.

The method may further comprise changing, e.g. reducing, the distance D1 between the catching component 20 (and/or the lateral groove 22 thereof) and the elongate flexible outer member 28. This may result in tissue, that is located between the lateral groove 22 and the elongate flexible outer member 28 (e.g. tissue of the circumferential valve tissue structure 6, e.g. a sub-annular portion thereof), being forced into the lateral groove 22 and being immobilized therein. In other words, the method may comprise immobilizing tissue using the catheter member 8 and the elongate flexible outer member 28 by reducing a distance between catheter member 8 and the elongate flexible outer member 28.

The method may further comprise placing a prosthesis, e.g. prosthesis 500 as described above, close to the annulus 4c of the heart valve 4, e.g. close to the annulus 4c on a side of the ventricular chamber 4a. Placement of the (or a) prosthesis may take place when the tissue is fully immobilized, substantially immobilized or when the tissue is not immobilized (i.e. after, while and/or before the distance D1 is reduced or at any other time). Specifically, placing the prosthesis 500 may comprise placing the prosthesis 500 on the elongate flexible outer member 28 so that the inner lumen 520 of prosthesis is received by the elongate flexible outer member 28 (this is schematically indicated in FIG. 14, wherein the elongate flexible outer member 28 is indicated by a dashed line 28 that is collinear with the longitudinal axis 510 of the prosthesis 500, however the prosthesis 500 may also be provided separate from the elongate flexible outer member 28). For example, the prosthesis 500 may be placed around the elongate flexible outer member 28 on a proximal end of the elongate flexible outer member 28 (e.g. at or close to the position of the catching mechanism 32) and may be moved in a distal direction of the elongate flexible outer member 28 towards the heart valve 4. The prosthesis 500 may then be placed on the elongate flexible outer member 28 at an intended position close to the annulus 4c. In other word, the method may comprise placing the prosthesis 500 on an intended position close to the annulus 4c (e.g. sub-annularly on a side of the ventricular chamber 4a) using the elongate flexible outer member 28 as a guiding means for precise placement, e.g. for precise placement on a circumference of the annulus 4c. Placing the prosthesis 500 may result in a situation in which tissue is immobilized by the elongate flexible outer member 28 inside the lateral groove 22 while the prosthesis is placed on the elongate flexible outer member 28 and is at least partially or fully located inside the lateral groove 22. According to aspects of the method, the distance D1 is only reduced when the prosthesis 500 is substantially placed on the elongate flexible outer member 28 as intended, as a movement of the prosthesis 500 may be easier when the distance D1 between catheter member 8 and outer member 29 is not fully reduced. However, due to a flexibility/elasticity of the catching component 20 (e.g. when it is formed as cage body 36), outer member 29, prosthesis 500 and/or biological tissue, the prosthesis 500 may also be placed on the intended position when the distance D1 is reduced and tissue is substantially fully caught and immobilized in the lateral groove 22. The distance D1 may also be reduced, so that tissue is partially caught in the lateral groove 22, then the prosthesis 500 may be placed on its intended position using the elongate flexible outer member 28 as a guide, and when the prosthesis 500 is placed as intended, the distance D1 may be further reduced to fully immobilize the tissue in the lateral groove 22. In this respect it is to be noted that a reduction of distance D1, may equal a reduction of the perimeter that the elongate flexible outer member 28 defines around the circumferential tissue structure 6 and/or increasing a diameter of catching component 20 (e.g. via radial expansion as described above with reference to FIG. 4). Accordingly, a dimension of prosthesis 500 that is located on the elongate flexible outer member 28 around circumferential tissue structure 6 may be changed together with a change of the perimeter that is defined by the elongate flexible outer member 28. Accordingly, by handling the elongate flexible outer member 28 and/or catheter member 8 (e.g. catching component 20, e.g. wire cage 36) to change the distance D1 between the elongate flexible outer member 28 and catheter member 8 (e.g. lateral groove 22), prosthesis 500 may be elastically and/or plastically deformed to assume an intended shape as defined e.g. by angle α, radius R1, length L and/or diameters D3 and D4 that may be favorable for annuloplasty or other treatment. Further, the method may comprise using other catheters or means (not shown) that may not be a part of treatment catheter system 2 to change a shape, size, rigidity or other characteristics of prosthesis 500 and/or to fixate prosthesis 500. That is, the prosthesis 500 may also be separate from the elongate flexible outer member 28 and may be guided to its intended position using means other than elongate flexible outer member 28.

The method may also comprise fixating the prosthesis to tissue of the valve 4, e.g. fixating the prosthesis 500 to tissue of the circumferential tissue structure 6 as a sub-annular prosthesis 500. Fixating the prosthesis 500 may comprise using the catheter member 8 and/or catching member 20 comprising the lateral groove 22 to push or move the prosthesis 500 that is located at least partially on the elongate flexible outer member 28 and inside the lateral groove 22 in a direction of the annulus 4c, e.g. in a direction from the ventricular chamber 4a towards the annulus 4c. In order to push or move the prosthesis 500 towards the annulus to be in close contact to tissue of the annulus 4c, the method may comprise pushing or moving the catheter member 8 in a distal direction of catheter member 8 so that the prosthesis 500, that is located at least partially in the lateral groove 22, is brought into close contact with tissue of the annulus 4c or tissue close thereto via a force that is exerted on the prosthesis 500 via the catheter member 8, catching component 20 and/or the lateral groove 22 (and optionally as well via tissue, that might be located inside the lateral groove 22 along with the elongate flexible outer member 28 and/or the prosthesis 500).

Fixating prosthesis 500 may be carried out when the prosthesis 500 is pushed against tissue as described above in order to improve contact between the tissue and the prosthesis 500. Fixating the prosthesis 500 may optionally also comprise permanently fixating the prosthesis 500. Permanently fixating may herein refer to fixating the prosthesis 500 so that it may remain in the heart after surgical treatment is finished and catheter member 8 and/or the elongate flexible outer member 28 are removed from the heart.

However, it does not necessarily imply that the connection between prosthesis 500 and tissue (e.g. annulus 4*c*) may not be reversible, e.g. during further surgical treatment. The prosthesis 500 may be permanently fixated using sutures, staples, hooks, clips or screws 530 as schematically shown in FIGS. 13*a* and *b*.

According to the present invention, the method step(s) of fixating (e.g. permanently fixating) the prosthesis 500 may be carried out before, while or after the distance D1 is reduced, which may also mean before, while or after prosthesis 500, that is at least partially located on the elongate flexible outer member 28, is elastically and/or plastically deformed as described above. Instead of fixating a prosthesis 500, any other treatment may be carried out when tissue of the valve 4 is immobilized by the treatment catheter system 2.

The method of carrying out surgical treatment may further comprise retracting the catheter member 8 and/or the elongate flexible outer member 28 (c.f. FIG. 13*b*). In FIG. 13*b*, the radial distance D1 between the elongate flexible outer member 28 and the catheter member 8 has been increased, releasing the (valve) tissue 6 caught and immobilized in the lateral groove 22. Then, the catheter member 8 is moved away from the vicinity of the valve 4. Moving the catheter member 8 away from the valve 4 may comprise moving the catheter member 8 and/or retracting the catching component 20 (e.g. cage body 36) at least partially or fully into the inner lumen 14 of catheter member 8. Eventually, the catheter member 8 may be removed completely from the body. Further, the elongate flexible outer member 28 may be removed from the valve 4. Removing the elongate flexible outer member 28 may comprise moving (e.g. pulling or pushing) elongate flexible outer member 28 through the inner lumen 520 of prosthesis 500 (that may be fixated to tissue). However, prosthesis 500 may remain fixated to the annulus 4*c* (e.g. using hooks, screws or clips 530 or the like).

Using the above described method or a part thereof of may allow prolonged surgical treatment of immobilized heart tissue as temporary artificial valve 42 may control blood flow during surgery while lateral groove 22 and the tissue caught therein may serve as a seal to block bloodflow bypassing the temporary artificial valve 42.

Any method described herein may also optionally comprise anesthetizing a patient for a substantially defined, continuous interval of time. Anesthetizing the patient for a continuous time interval may be the first step of any method of using the treatment catheter system 2. Further, in any method that is described herein, placement of the lateral groove 22 (i.e. of the catheter member 8) and the elongate flexible outer member 28 close to a bloodstream valve 4, as well as treatment of tissue using the treatment catheter system 2 (e.g. fixing a prosthesis 500 to the valve 4) and removal of catheter member 8 and/or the elongate flexible outer member 28 (and e.g. outer member catheter 29) from the patient may be carried out during said continuous time interval.

Further, any method herein may comprise aligning the longitudinal axis 12 of catheter member 8 (e.g. catching component 20, e.g. cage body 36) and the axial direction 4*d* that is defined between two heart chambers so that they are substantially parallel to each other and or are collinear.

While a method for surgical treatment using a prosthesis and a method for placing an anchor 50 have been described independently, according to the present invention anchor 50 and prosthesis 500 may be placed and/or fixated at the same time. Accordingly, a method of using a treatment catheter 2 according to the present invention may comprise any combination or sub-combination of the method steps described herein as well as of method steps that are not explicitly disclosed as method steps but rather as physical features of treatment catheter system 2. Accordingly, any use or interaction of a physical feature of treatment catheter system 2 may also be a method step for a method of using the treatment catheter system 2 and vice versa.

What is claimed is:

1. A treatment catheter system for treatment of a bloodstream valve having a circumferential valve tissue structure, comprising
    an elongate catheter member to be disposed at the interior of the circumferential valve tissue structure and to be removed therefrom after treatment, the elongate catheter member extending along a longitudinal axis and having an inner lumen and proximal and distal end portions, the elongate catheter member comprising
        a catching component that is formed by a cage and is or can be positioned at the distal end portion of the elongate catheter member and is non-separable from the elongate catheter member at least when being positioned at the distal end portion of the elongate catheter member, and that at least when being positioned at the distal end portion of the elongate catheter member comprises a lateral groove provided as a circumferential groove formed in an outer circumferential surface of the cage, the lateral groove extending transverse to the longitudinal axis and opening to a lateral outer side so as to form a lateral catching opening,
    an elongate flexible outer member to be disposed at the exterior of the valve structure at a level of the lateral groove, the elongate flexible outer member being capable of at least partially extending circumferentially around the catheter member with valve tissue of the circumferential valve tissue structure being correspondingly circumferentially arranged between the elongate catheter member and the elongate flexible outer member, and
    a catching mechanism operable to reduce a radial distance between the elongate catheter member and the elongate flexible outer member so as to catch at least part of the valve tissue between the outer member and the elongate catheter member within the lateral groove via the catching opening to thereby immobilize the caught valve tissue on the distal end portion of the elongate catheter member.

2. The treatment catheter system according to claim 1, wherein the catching component is moveable relative to the elongate catheter member and can be forwarded and retracted or otherwise exposed via the inner lumen of the elongate catheter member.

3. The treatment catheter system according to claim 1, wherein the catching component is integrally formed with the elongate catheter member at the distal end portion of the elongate catheter member.

4. The treatment catheter system according to claim 1, wherein the cage is provided to be radially compressible and expandable so that it can be accommodated within the inner lumen of the elongate catheter member in a radially compressed condition and can be expanded or self-expands at the distal end portion of the elongate catheter member.

5. The treatment catheter system according to claim 4, wherein the wires are connected to each other by a substantially non-compressible front body having a rounded outer side and having an outer diameter slightly larger than an inner cross-sectional diameter of the lumen of the elongate catheter member to be able to provide a plug for closing a frontal end opening of the inner lumen of the elongate catheter member.

6. The treatment catheter system according to claim 1, wherein the cage is formed by a plurality of elongate wires substantially extending along the longitudinal axis of the elongate catheter member and being angularly spaced around the longitudinal axis of the elongate catheter member, the elongate wires each comprise a radially and inwardly bended bending portion, the bending portions forming the lateral groove.

7. The treatment catheter system according to claim 6, wherein each wire is provided in and moveable relative to a sheath which is provided in the lumen of the elongate catheter member and moveable relative to the elongate catheter member.

8. The treatment catheter system according to claim 1, wherein the catching component comprises a blunt front part.

9. The treatment catheter system according to claim 1, further comprising an elongate flexible perforation component which can be forwarded through the inner lumen of the elongate catheter member to the distal end portion of the elongate catheter member and which is operable such as to provide a perforation through the valve tissue caught in the lateral groove or through valve tissue adjacent to the caught valve tissue.

10. The treatment catheter system according to claim 9, wherein the perforation component is formed by a needle which is provided and arranged such as to be forwarded into the lateral groove.

11. The treatment catheter system according to claim 9, further comprising an anchor component which can be forwarded through the inner lumen of the elongate catheter member and can be placed within the caught valve tissue or within adjacent valve tissue, wherein
the perforation component is hollow, and
the anchor component is provided such that it can be forwarded through the perforation component to the distal end portion of the elongate catheter member.

12. The treatment catheter system according to claim 1, further comprising an anchor component which can be forwarded through the inner lumen of the elongate catheter member and can be placed within the caught valve tissue or within adjacent valve tissue.

13. The treatment catheter system according to claim 12, further comprising a chord attached to the anchor component.

14. The treatment catheter system according to claim 1, further comprising a medical drug supplying component which is provided such that it can be forwarded through the inner lumen of the elongate catheter member to the distal end portion of the elongate catheter member and such that it can forward a medical drug to the caught valve tissue or the adjacent valve tissue.

15. The treatment catheter system according to claim 14, further comprising an elongate flexible perforation component which can be forwarded through the inner lumen of the elongate catheter member to the distal end portion of the elongate catheter member and which is operable such as to provide a perforation through the valve tissue caught in the lateral groove or through valve tissue adjacent to the caught valve tissue, wherein the perforation component is hollow, and
the medical drug supplying component is provided such that it can be forwarded to the distal end portion of the elongate catheter member through the perforation component.

16. The treatment catheter system according to claim 1, further comprising marker members fixedly attached on the catheter member and the elongate flexible outer member, wherein the marker members are made from a material different than the material of the elongate catheter member and outer member respectively, to allow identifying relative positions and orientations of the elongate catheter member and the elongate flexible outer member using material-sensitive imaging techniques.

17. The treatment catheter system according to claim 1, wherein
the catching component and the elongate flexible outer member each comprise an electrode which is electrically connected to an electric energy source, and
the electrodes of the catching component and the elongate flexible outer member selectively produce an electric field between each other using electric energy supplied from the energy source to open holes in cell membranes of the valve tissue.

18. The treatment catheter system according to claim 1, wherein the catching component is provided with an artificial heart valve.

19. The treatment catheter system according to claim 1, wherein
the elongate flexible outer member is provided with a prosthesis having an inner lumen that at least partially receives the elongate flexible outer member to be slideable along a longitudinal direction of the elongate flexible outer member, and
the prosthesis is configured to be fixated to the bloodstream valve.

20. The treatment catheter system according to claim 19, wherein
the prosthesis has an outer cross-sectional diameter that is defined in a radial direction of a longitudinal axis of the prosthesis, that is smaller than a width of the lateral groove in a direction of the longitudinal axis of the elongate catheter member.

21. A method for surgical treatment of a bloodstream valve having a circumferential valve tissue structure, the method comprising:
advancing the treatment catheter system according to claim 1 into a vicinity of the bloodstream valve;
placing the lateral groove of the catheter member in an interior of the circumferential valve tissue structure;
placing the elongate outer member at least partially around an outside of the circumferential tissue structure at an axial level, with respect to the longitudinal axis, of the lateral groove;
reducing a distance between the elongate outer member and the lateral groove so as to at least partially force tissue of the circumferential valve tissue structure into the lateral groove; and
removing the catheter member and the elongate outer member from the patient.

22. A treatment catheter system for treatment of a bloodstream valve having a circumferential valve tissue structure, comprising
an elongate catheter member to be disposed at the interior of the circumferential valve tissue structure and to be removed therefrom after treatment, the elongate catheter member extending along a longitudinal axis and having an inner lumen and proximal and distal end portions, the elongate catheter member comprising
  a catching component that is provided with an artificial heart valve and is or can be positioned at the distal end portion of the elongate catheter member and is non-separable from the elongate catheter member at least when being positioned at the distal end portion of the elongate catheter member, and that at least when being positioned at the distal end portion of the elongate catheter member comprises a lateral groove that extends transverse to the longitudinal axis and that opens to a lateral outer side so as to form a lateral catching opening,
  an elongate flexible outer member to be disposed at the exterior of the valve structure at a level of the lateral groove, the elongate flexible outer member being capable of at least partially extending circumferentially around the catheter member with valve tissue of the circumferential valve tissue structure being correspondingly circumferentially arranged between the elongate catheter member and the elongate flexible outer member, and
  a catching mechanism operable to reduce a radial distance between the elongate catheter member and the elongate flexible outer member so as to catch at least part of the valve tissue between the outer member and the elongate catheter member within the lateral groove via the catching opening to thereby immobilize the caught valve tissue on the distal end portion of the elongate catheter member.

23. The treatment catheter system according to claim 22, wherein the catching component is formed by a tubular sleeve having a lateral cutout extending in a transverse direction of the longitudinal axis of the elongate catheter member and forming the lateral groove.

24. A method for surgical treatment of a bloodstream valve comprising a circumferential valve tissue structure of a patient using the treatment catheter system according to claim 22, the method comprising
  placing the lateral groove of the catheter member in an interior of the circumferential valve tissue structure,
  placing the elongate outer member at least partially around an outside of the circumferential tissue structure at an axial level, with respect to the longitudinal axis, of the lateral groove,
  reducing a distance between the elongate outer member and the lateral groove so as to at least partially force tissue of the circumferential valve tissue structure into the lateral groove, and
  removing the catheter member and the elongate outer member from the patient.

25. The method according to claim 24, wherein
  the blood stream valve is a mitral valve connecting a ventricular chamber with an atrial chamber and having a valve annulus and the circumferential valve tissue structure on a side of the ventricular chamber, and wherein
  placing the lateral groove comprises placing the lateral groove in the ventricular chamber close to the annulus.

26. The method according to claim 25, wherein
  the ventricular-chamber and the atrial chamber define an axial direction therebetween, wherein
  the treatment catheter system further comprises a prosthesis having an inner lumen at least partially receiving the elongate outer member, and wherein
  reducing the distance comprises forcing at least a part of the prosthesis into the lateral groove, and wherein
  the method further comprises moving the lateral groove in an axial direction of the valve towards the annulus so that the prosthesis is in close contact with the annulus, and
  fixing the prosthesis to the annulus.

* * * * *